US009002428B2

(12) United States Patent
Mazer et al.

(10) Patent No.: US 9,002,428 B2
(45) Date of Patent: Apr. 7, 2015

(54) METHODS FOR DETECTING ABNORMALITIES AND DEGENERATIVE PROCESSES IN SOFT TISSUE USING MAGNETIC RESONANCE IMAGING (MRI)

(75) Inventors: Aviv Mazer, Stanford, CA (US); Robert Dougherty, Menlo Park, CA (US); Brian Wandell, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 365 days.

(21) Appl. No.: 13/360,714

(22) Filed: Jan. 28, 2012

(65) Prior Publication Data

US 2012/0197105 A1     Aug. 2, 2012

Related U.S. Application Data

(60) Provisional application No. 61/437,587, filed on Jan. 28, 2011.

(51) Int. Cl.
*A61B 5/055*     (2006.01)
*G01R 33/50*    (2006.01)
*A61B 5/00*     (2006.01)
*A61B 5/107*    (2006.01)

(52) U.S. Cl.
CPC ............... *A61B 5/055* (2013.01); *A61B 5/0042* (2013.01); *A61B 5/1073* (2013.01); *G01R 33/50* (2013.01)

(58) Field of Classification Search
CPC ...................................................... G01R 33/50
USPC ......................................................... 600/410
See application file for complete search history.

(56) References Cited

U.S. PATENT DOCUMENTS

2009/0312625 A1\* 12/2009 Du ................................ 600/410
2010/0127704 A1\*  5/2010 Warntjes ...................... 324/309

\* cited by examiner

*Primary Examiner* — Jonathan Cwern
(74) *Attorney, Agent, or Firm* — Andrea Blecken

(57) ABSTRACT

The present invention provides methods to detect degenerative processes and abnormalities in soft tissues at high spatial resolution, high signal-to-noise ratio and short scanning times, based on quantitative tissue properties. These methods might provide a useful tool to detect and assess abnormalities in soft tissues and to monitor disease progression.

14 Claims, 11 Drawing Sheets

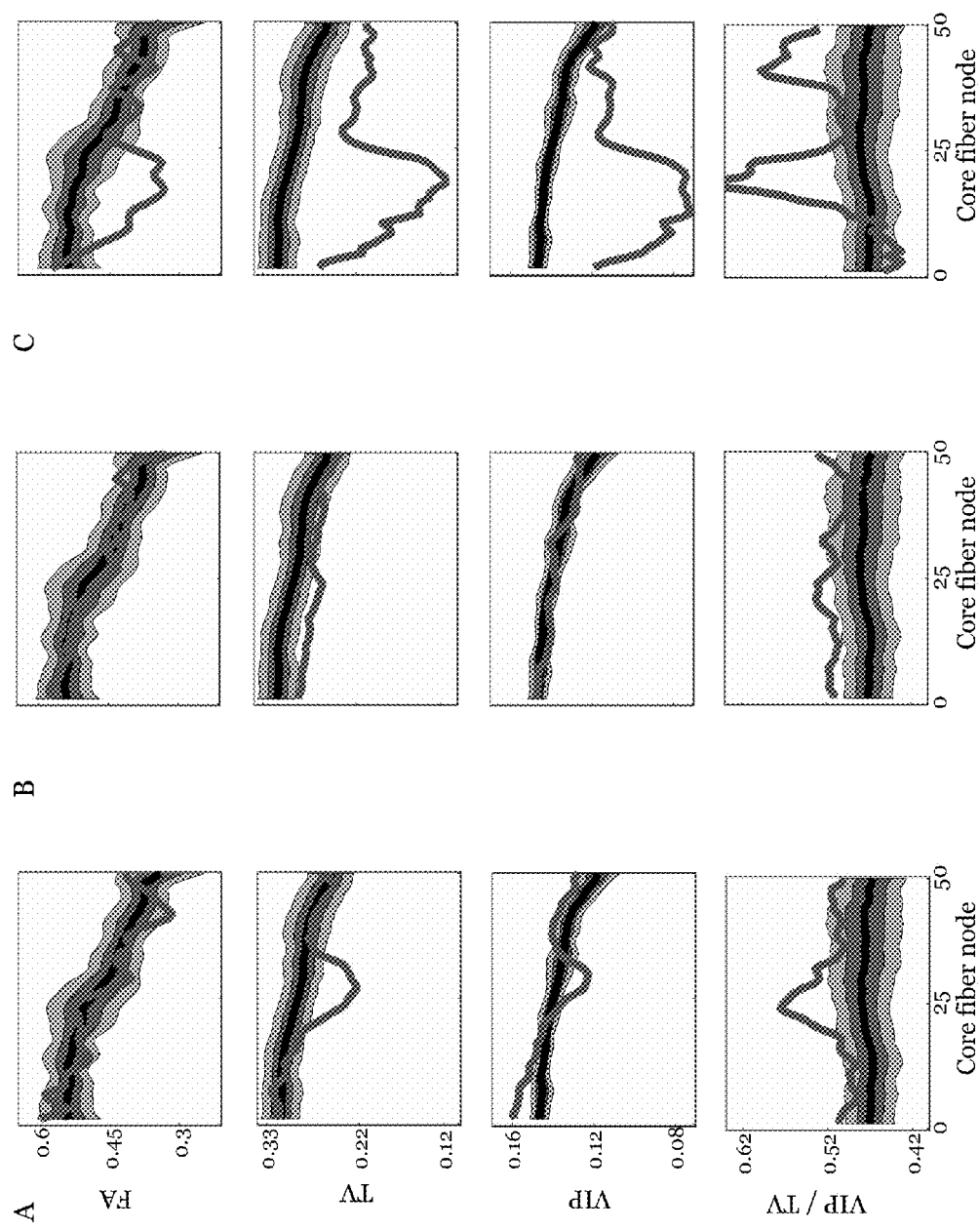

METHODS FOR DETECTING ABNORMALITIES AND DEGENERATIVE PROCESSES IN SOFT TISSUE USING MAGNETIC RESONANCE IMAGING (MRI)

RELATED APPLICATION

This application claims priority and other benefits from U.S. Provisional Patent Application Ser. No. 61/437,587, filed Jan. 28, 2011, entitled "Improved methods for detecting abnormalities in soft tissue using magnetic resonance imaging (MRI)". Its entire content is specifically incorporated herein by reference.

STATEMENT OF GOVERNMENT SUPPORT

This invention was made with government support under EY015000 awarded by the National Institutes of Health. The government has certain rights in the invention.

TECHNICAL FIELD OF THE INVENTION

The present invention relates generally to the study of neurological disorders. More specifically, it relates to the use of magnetic resonance imaging (MRI) and quantitative tissue properties to study soft tissues, particularly brain tissue, to detect abnormalities and degenerative processes.

BACKGROUND

Magnetic resonance imaging (MRI) is a valuable and increasingly popular, diagnostic technique in clinical applications for noninvasively imaging soft body tissues such as the brain to visualize internal structures and to study neural development.

Functional neuroimaging techniques, including positron emission tomography and functional MRI (fMRI) such as BOLD imaging, are primarily based on qualitative measures, and often require group averages to show any differences in tissue structure or development. If differences are detected, it is often difficult to establish a biological basis and relate such differences to clinical applications. Furthermore, inconveniently long scanning times of one hour or more, complex processing, calculations or interpretation and low-resolution images of qualitative approaches can hamper a reliable and accurate detection of structural changes such as degenerative processes, as it is needed for early detection, prognosis and diagnosis.

Using quantitative tissue properties in neuroimaging and applying them in biophysical tissue models is increasingly important to advancing our ability to study neural development, to differentiate diseased neuronal tissues from typical, disease-free tissues and to understand the structure and function of key pathways in the human brain.

The present invention addresses this need.

SUMMARY

Improved methods for detecting structural abnormalities and degenerative processes in soft tissues based on biophysical tissue models derived from quantitative tissue properties are provided. The non-water tissue volume (TV) and volume of interacting protons with the tissue (VIP) in soft tissue are quantitative tissue properties that are useful for building biophysical tissue models to study soft tissues with respect to development, microstructure and key pathways. The volumes measurements in different volumes of interest in a subject's soft tissue such as the brain is determined using specialized algorithms that combine proton density (PD) and T1 map data and that allow the calculation of water-pools and non-water-pools in the imaged tissue.

In one aspect, the microstructure of soft tissue in a subject is non-invasively imaged using magnetic resonance and magnetic resonance imaging parameters including longitudinal relaxation time T1 and proton density are acquired. The non-water tissue volume and volume of interacting protons are determined to quantify the volume and exposed surface area of cell membranes and macromolecules in the soft tissue and compared to soft tissue from a control subject to evaluate for the presence of abnormalities or degenerative processes. Soft tissues in the various embodiments include cartilage, fatty tissue, muscle tissue, peripheral as well as central nerve tissue.

In one embodiment, the microstructure of brain white matter in a subject is non-invasively imaged using magnetic resonance and magnetic resonance imaging paramaters including longitudinal relaxation time T1 and proton density are acquired. The non-water tissue volume and volume of interacting protons are determined to quantify the volume and exposed surface area of cell membranes and macromolecules in the brain gray and white matter and compared to brain gray and white matter from a control subject to evaluate for the presence of abnormalities or degenerative processes. In one particular embodiment, the non-water tissue volume and volume of interacting protons are determined to quantify the volume and exposed surface area of cell membranes and macromolecules in the brain gray and white matter from children in comparison to adults and utilized to evaluate for normal or abnormal brain development.

In a particular aspect of the invention, the tissue volume and volume of interacting protons is determined in brain white matter as a measure of myelin content, and the myelin contents of different areas in the brain are compared. In one embodiment, the abnormalities or degenerative processes are indicative of a demyelination disease, such as multiple sclerosis, and the methods are used to diagnose a demyelination disease in a subject compared to a healthy control subject. In another embodiment, the abnormalities or degenerative processes are indicative of a demyelination disease and the methods are used repeatedly within a certain time period to monitor a subject's response to treatment of a demyelination disease. In another embodiment, the abnormalities or degenerative processes are indicative of abnormal brain development and the methods are used to diagnose and monitor abnormal brain development; the methods can also be used to correlate in a subject with diagnosed abnormal brain development the subject's brain gray and white matter microstructure with cognitive abilities such as reading ability or writing ability in said subject. In a further embodiment, the abnormalities or degenerative processes are indicative of abnormal aging processes and the methods are used to diagnose and monitor abnormal aging processes. In another embodiment, the abnormalities or degenerative processes are indicative of a neurodegenerative disease, such as Alzheimer's Disease, and the methods are used to diagnose and monitor a neurodegenerative disease; the methods can also be used to correlate in a subject with a diagnosed neurodegenerative disease the subject's brain gray and white matter microstructure with cognitive abilities in said subject. In another embodiment, the abnormalities or degenerative processes are indicative of a neurological disease, such as Autism, and the methods are used to diagnose and monitor a neurological disease; the methods can also be used to correlate in a subject with a diagnosed neurological disease the subject's brain gray and white matter microstructure with cognitive abilities in said subject. In a further embodiment, the abnormalities or degenerative processes are indicative of a metabolic disease, such as Type I and Type II diabetes mellitus, and the methods are used to diagnose and monitor a metabolic disease.

In another aspect, the microstructure of various brain tissue of a subject is non-invasively imaged using magnetic resonance and magnetic resonance imaging parameters including longitudinal relaxation time T1 and proton density are acquired. The non-water tissue volume and volume of interacting protons are determined to quantify the volume and exposed surface area of cell membranes and macromolecules in the brain tissue and utilized to classify said brain tissue into white matter, gray matter and cerebrospinal fluid.

In a further aspect, the microstructure of brain white matter in a subject is non-invasively imaged using magnetic resonance and magnetic resonance imaging parameters including longitudinal relaxation time T1 and proton density are acquired. The non-water tissue volume and volume of interacting protons are determined to quantify the volume and exposed surface area of cell membranes and macromolecules in the brain white matter and utilized to characterize white matter tracts and to distinguish said tracts from neighboring white matter.

In a further aspect, the microstructure of brain gray matter in a subject is non-invasively imaged using magnetic resonance and magnetic resonance imaging parameters including longitudinal relaxation time T1 and proton density are acquired. The non-water tissue volume and volume of interacting protons are determined to quantify the volume and exposed surface area of cell membranes and macromolecules in the brain gray matter and utilized to characterize gray matter region and to distinguish from neighboring gray matter.

To calculate the non-water tissue volume and volume of interacting protons RF-coil corrections are developed. Both the receive and excite correction may be used to improve MR imaging homogeneity quality. The receive in-homogeneity mapping can also be used to achieve improved parallel imaging (fast MRI exaction) as this method depends on receive in-homogeneity knowledge.

The above summary is not intended to include all features and aspects of the present invention nor does it imply that the invention must include all features and aspects discussed in this summary.

INCORPORATION BY REFERENCE

All publications mentioned in this specification are herein incorporated by reference to the same extent as if each individual publication was specifically and individually indicated to be incorporated by reference.

BRIEF DESCRIPTION OF THE DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

FIG. 11 shows the diffusion fractional anisotropy (FA), tissue volume (TV), volume of interacting protons (VIP) and VIP/TV ratio values along the white matter tract Inferior longitudinal fasciculus (ILF) for three MS subjects (A, B and C) and 16 control subjects, as further detailed in Example 3. Each MS subject's FA, TV, VIP and VIP/TV values (red line) are shown in a different column in comparison to the values of the control subjects. The normal population values (10-90 percentile) along that tract are marked in gray. While the control subjects have a tight distribution of FA, TV, VIP and VIP/TV values, the MS subjects exhibit clearly distinguishable differences along the tract compared to the control subjects.

DETAILED DESCRIPTION

Figure 1:
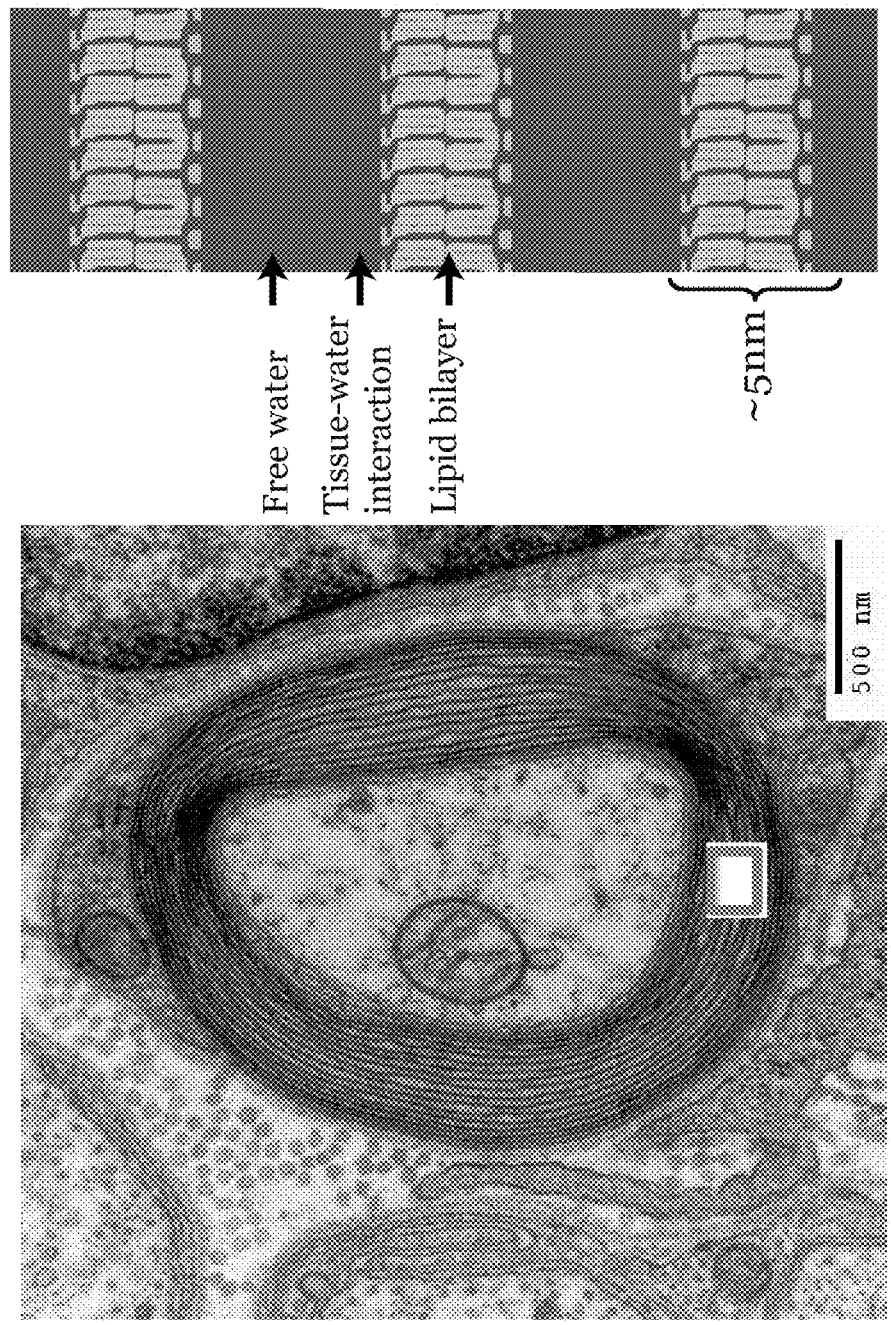
FIG. 1 shows the spatial relationship between the lipid bilayer tissue volume (TV) and volume of interacting protons (WIP) and free water. The figure defines the three tissues compartment that affects the MR signal in human tissue like the white matter. An example for white matter tissue taken with electro-microscopy is shown in the right. The non water tissue reduce the maximum MRI signal. The free water proton and the with the tissue have a different T1 MR relaxation constant. The dependency on the magnetic field and temperature dependence of T1 values differ significantly between the two water proton compartments. These differences, which arise from physical interactions at very small length scales, can be measured in the bulk magnetization signal measured at the scale of the MRI voxel (~1 mm), as further detailed in Example 1.

Before describing detailed embodiments of the invention, it will be useful to set forth definitions that are utilized in describing the present invention.

1. Definitions

The practice of the present invention may employ conventional techniques of magnetic resonance imaging, which are within the capabilities of a person of ordinary skill in the art. Such techniques are fully explained in the literature. For definitions, terms of art and standard methods known in the art, see, for example, Paul Tofts "Quantitative MRI of the brain: measuring changes cause by disease", John Wiley & Sohns, 1st edition (2003), which is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable. As used herein, the singular forms "a" and "the" include plural referents, unless the context clearly dictates otherwise.

The term "subject", as used herein, refers to a member of a species of mammalian origin, particularly to a human being.

The term "voxel", as used herein, denotes a volume element that corresponds to a discrete image element (pixel) and is used to express a quantity in a unit per volume of tissue.

The term "flip angle", as used herein, defines the amount of rotation of the macroscopic magnetization vector produced by a radiofrequency pulse, where longitudinal magnetization is tipped towards the transverse plane.

The term "spatial resolution", as used herein, defines the smallest distance between two points in an object that can be distinguished as separate details on an image.

Magnetic resonance imaging (MRI) is a valuable technique to noninvasively image body tissues such as the brain based on the electromagnetic activity of atomic nuclei. Nuclei consist of protons and neutrons, both of which have spins and can induce their own magnetic field through their motion. Clinically, hydrogen nuclei (water protons) are most often used because of their abundance in the body and because they are the most convenient molecular species to study.

MRI is carried out by exciting protons in a uniform magnetic field out of their low-energy equilibrium state through a radiofrequency (RF) pulse and measuring electromagnetic radiation that is released while the protons decay back to the low-energy equilibrium level. In an MRI scanner a radiofrequency transmitter is used to produce an electromagnetic field, whereby the strength of the magnetic field is influenced by the intensity and the duration of the radiofrequency. When the body is subjected to a magnetic field within an MRI scanning machine, some protons get excited, their electromagnetic moments change and align with the direction of the external magnetic field, i.e., their spin direction gets flipped. Once the external magnetic field is turned off, the excited protons decay to their original equilibrium spin state, thereby releasing the differential energy as photons. It is these photons that produce the electromagnetic signal that the MRI scanning machine ultimately detects (MR signal). Since the protons in different tissues return to their equilibrium state at different rates, an image can be constructed. In the course of this process, MRI scanners generate multiple two-dimensional cross sections or slices of tissue and reconstruct 2- or 3-dimensional imagines that can provide valuable information about the local tissue environment and potentially provide diagnostic indication of pathological conditions in a particular region of interest.

An MRI system typically consists of several components: a) a magnet to produce a magnetic field; b) coils to make the magnetic field homogenous; c) a radiofrequency transmitter (radiofrequency coil) to transmit a radio signal into the body part or tissue being imaged; d) a receiver coil to detect the returning radio signals; e) gradient coils to provide spatial localization of the radio signals; f) a computer-readable medium or computer to reconstruct the radio signals into an MRI image using specific algorithms.

The body is primarily composed of water molecules which carry two protons per molecule, each proton having its own electromagnetic moment (magnetic dipole moment) which is a measure of its tendency to align with a magnetic field. In current practice MRI signals measure a combination of physical effects that depend on the particular tissue's proton density and that reflect the interaction of protons with their local environment. Proton density (PD) denotes the concentration of protons in the tissue in form of water and macromolecules such as proteins or fats and defines the maximal amplitude of a radio signal, since protons, as the resonating hydrogen nuclei, cause the nuclear magnetic resonance signal. The higher the density of protons in a particular volume of tissue, the larger is the resulting signal. For example, a signal from CSF, which has a high proton density, is larger than a signal from white matter brain in which about 30% of the volume is filled with macromolecules, in particular with myelin. As broadly accepted in the art, the ratio of proton density in CSF:gray matter:white matter is about 100:82:70, as summarized by Tofts, 2003.

Tissue specific MRI parameters such as proton density, longitudinal relaxation time T1 and transverse relaxation T2 affect the intensity of a magnetic resonance image and can be evaluated independently or in combination. T1, T2 and the proton density are important intrinsic biophysical properties of biological tissues and valuable components for biophysical tissue models that are useful for characterizing tissues and for, e.g., detecting tissue abnormalities. T1, T2 and the proton density, thus, represent important parameters in MRI for differentiating between different neuronal tissues and for differentiating typical from atypical, pathological or degenerated tissue. Proton density measurements are, for example, useful for estimating water content in the context of, e.g., the course of a disease and its response to treatment. Variable image contrast can be achieved by varying pulse sequences and/or imaging parameters. Pulse sequence parameters determine the number, strength and timing of radiofrequency pulses. The recovery to the low-energy equilibrium level is exponential with T1, T2, and their corresponding relaxation rates $R_1=1/T1$ and $R_2=1/T2$. These time constants may depend on the magnetic field, on the temperature and the local environment of protons in a particular tissue.

T1 denotes a characteristic time constant for longitudinal relaxation (return of an excited system of spinning particles to its equilibrium state) with which, following excitation by a radiofrequency pulse, magnetization along the static magnetic field returns to its equilibrium value. The longitudinal relaxation time of unbound water, "free water", is on the order of a few seconds, while the relaxation time of water molecules that are attached to solids, "bound water", as it is the case in the hydration layer, is typically smaller than a second. The protons in free water and bound water can exchange positions, and this exchange takes place at a rate that is a lot faster than either of the T1 values of free or bound water. Therefore, the measured longitudinal relaxation rate $R1=1/T1$ from a voxel containing macromolecules is a weighted sum of these two signals (Bottomley et al., 1984). In order to produce an image that depends strongly on T1, an inversion recovery (IR) sequence can be used, wherein the magnetization is inverted at a time on the order of T1. Measuring $T_1$ using an inversion recovery (IR) sequence typically requires a long scan time (as reviewed by Tofts, 2003). This sequence includes several repeats with different inversion times until a Gaussian curve with the $T_1$ time constant can be fitted. Spoiled gradient recalled echo (SPGR) acquisition in steady state is an alternative for T1 mapping; in this method a 3D image can be acquired quickly and $T_1$ can be estimated from the signal equation using methods known in the field (Deoni et al., 2004).

The term "T1 map data", as used herein, is a measure for the longitudinal relaxation time constants (T1) throughout the brain.

T2 denotes a characteristic time constant for transverse relaxation with which, following excitation by a radiofrequency pulse, magnetization decays orthogonal to the static magnetic field. Transverse relaxation happens usually faster than longitudinal relaxation. T2 depends on the interactions between protons in several water pools, each with their own time constants. Protons in non-water environments (e.g., lipids and macromolecules) often have short T2 values and are, therefore, often invisible to magnetic resonance imaging. Measuring multi-exponential T2 parameters requires many scan repeats with a range of parameters, as reviewed by Tofts, 2003.

Pulse sequences. Pulse sequences are wave forms of the gradients and radiofrequency pulses applied in MR image acquisition; they can be adjusted to measure a variety of biophysical properties of tissue and can be two-dimensional or three-dimensional. Spin echo imaging and gradient echo imaging are the two main types of pulse sequences.

In spin echo imaging, a slice-selective radiofrequency pulse is followed by a series of refocusing radiofrequency pulses, while the magnetic field is kept constant. The flip angle of the radiofrequency pulses is usually at or close to 90 degrees. The pulse sequence timing can be T1-weighted, T2-weighted or proton density-weighted. T1-weighted and T2-weighted spin-echo sequences are among the most common pulse sequences. Two important parameters in spin echo imaging are repetition time (TR) and echo time (TE). TR is the time between consecutive radiofrequency pulses, while TE is the time between the start of a radiofrequency pulse and the maximum peak in the signal. Only at short TRs, the difference in relaxation time between fat and water can be detected, since the longitudinal magnetization recovers more quickly in fat than in water. Only at long TEs, differences in the T2 signal decay in fat and water can be detected.

TR relates to T1 and affects contrast on T1-weighted images where T1 contrast is accentuated. Accordingly, the T1-weighted sequence uses a short TR<1000 msec and a short TE<30 msec, while the T2-weighted sequence uses a long TR>2000 msec and a long TE>80 msec. TE relates to T2 and affects contrast on T2-weighted images where T2 contrast is accentuated. Proton-density weighting is achieved with a long TR>2000 msec and short TE<30 msec.

In gradient echo imaging, the strength of the external magnetic field is varied following the application of a single, slice-selective radiofrequency pulse. Three types of gradients are applied, according to the axis of imaging (x-, y-, and z-) and sections of the tissue are imaged in accordance to the applied gradient. A phase-encoding gradient causes a phase shift. The flip angle of the radiofrequency pulse can range from 10 to 80 degrees. T2*-weighted MRI ("T2 star") scans use a gradient echo sequence, with long TR and long TE. The gradient echo sequence does not have the extra refocusing pulse used in spin echo, so it is subject to additional losses above the normal T2 decay (referred to as $_2$" "T2 star") scans use a gradient echo T2*. This also makes it more prone to susceptibility losses at air/tissue boundaries, but can increase contrast for certain types of tissue, such as venous blood.

Protons in macromolecules as well as protons in water molecules that are bound to macromolecules are typically not visible in an MRI scan due to their very short T2 relaxation time. In magnetization transfer (MT), an off-resonance radiofrequency pulse is used to saturate protons in macromolecules as well as protons in water molecules that are bound to macromolecules, which leads to an energy exchange between non-water protons and water protons. It is possible to introduce a specific excitation sequence to amplify the MT effect and measure the energy exchange, when data from an MT sequence are combined with data from T1 or T2 sequences (Tofts, 2003).

The number and properties of the proton pools in a brain voxel depend on the characteristics of the local brain tissue and the type of measurement (T1, T2 or MT). Two MRI techniques, the bound pool fraction and the multiple pools measurements, are conventionally used to quantify the size of the different water pools in brain voxels.

Imaging phantoms and phantoms, as used herein, are specially designed objects that serve as a substitute for a living subject and that are imaged by magnetic resonance to evaluate, analyze, and tune the performance of various imaging devices.

The bound pool fraction (BPF) method uses a quantitative magnetic transfer (MT) pulse sequence and a computational model to estimate the non-water protons bound to the macromolecules. The method measures the change in the magnetic relaxation when MT pulses at different strengths are added to a fixed MR sequence (Yarnykh & Yuan, 2004). There are two major disadvantages of the BPF method: first, the need for an MT sequence significantly increases the total scan time and so reduces its applicability in clinical settings. Only low-resolution MT images can be acquired in standard scanning times. Secondly, the BPF is derived from a model fit that estimates several parameters. The fitted parameters are not separable, the estimates depend significantly on measurement noise and the statistics of the fits to the key parameters are poorly understood.

Measurement of the multiple pools contributing to the T2 relaxation provides estimates of several pools; in white matter one of these is most likely myelin-dependent. The size of this particular T2 pool is called the myelin water fraction (MWF). The measurement is based on a 32 echo T2 relaxation curve. The relaxation curve is fit by an arbitrary number of exponential components using a non-negative least squares algorithm. The analysis returns several (typically three) T2 constants that are attributed to the different water pools. These are: the myelin water fraction with a T2 of ~20 ms, the cytoplasmic and extracellular fraction with a T2 of ~80 ms and the CSF with a T2 of <1000 ms images (Whittall et al., 1997).

Myelin water fraction. The myelin water fraction (MWF) is derived by fitting the T2 relaxation curve to a model comprising multiple exponential components. The analysis typically estimates three T2 constants that are attributed to different tissue environments. The fast decay signal is thought to represent the myelin water fraction (Mackay et al., 1994). This method requires many acquisitions and thus a relatively long time to estimate the T2 relaxation function for a full brain scan. Deoni et al. (Deoni et al., 2008) proposed a fast scanning method and fitting model, involving both T1- and T2-weighted images, to calculate the MWF. Deoni et al. (Deoni et al., 2008) report that the MWF estimates using the fast method are comparable to the estimates derived by MacKay and colleagues (Mackay et al., 1994). Several articles provide tabulated data describing MWF, T1 and PD in 20 brain regions of interest (ROIs) in normal and MS patients. Herein, the volume of interacting protons (VIP) formula was applied to the tabulated proton density (PD) and longitudinal relaxation time T1 data to estimate the VIP for each of these regions of interest (ROIs). This enabled a direct comparison between VIP and MWF. For the 20 ROIs, there was a correlation (r) of 0.652 (p<0.002) between the VIP and the MWF values.

Diffusion imaging. Diffusion imaging is a quantitative, widely used biophysical measure of brain structure that allows the non-invasive mapping of the diffusion process of molecules, primarily of water, in biological tissues producing various maps (Basser et al., 1994; Moseley at al., 1990). Diffusion (by Brownian motion) measures the statistics of water displacement and provides information about the orientation of the nearby membrane boundaries. This information can be useful to diagnose tissue abnormalities at a local scale. In an isotropic medium such as cerebrospinal fluid, water molecules move in all direction at an equal rate. If a medium is anisotropic, water molecules move at different rates.

Figure 7:
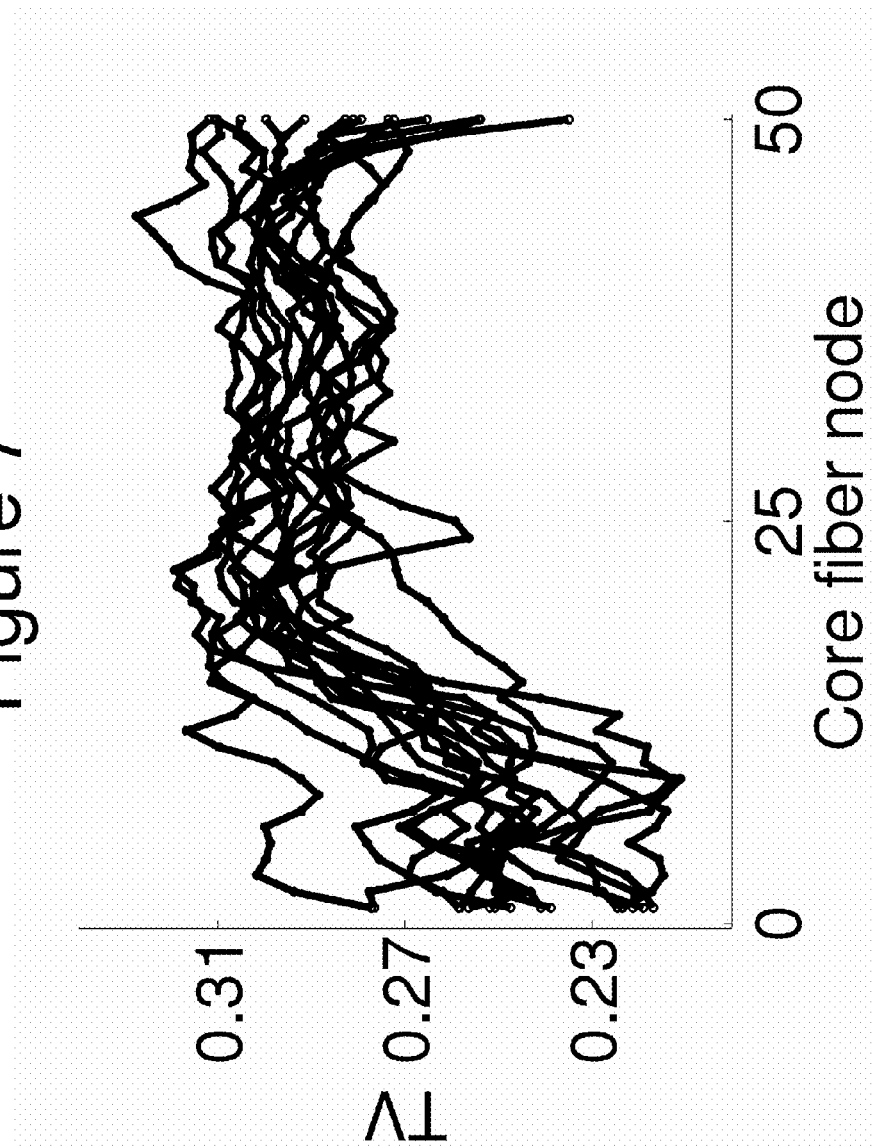
FIG. 7 shows the tissue volume (TV) values as measured at different positions along the CST in 16 different subjects (same subjects as investigated in FIG. 6), as further detailed in Example 2. The red line marks the location where the CST and callosal fibers intersect and FA values decline. Notice the consistent TV difference between subjects.
Figure 8:
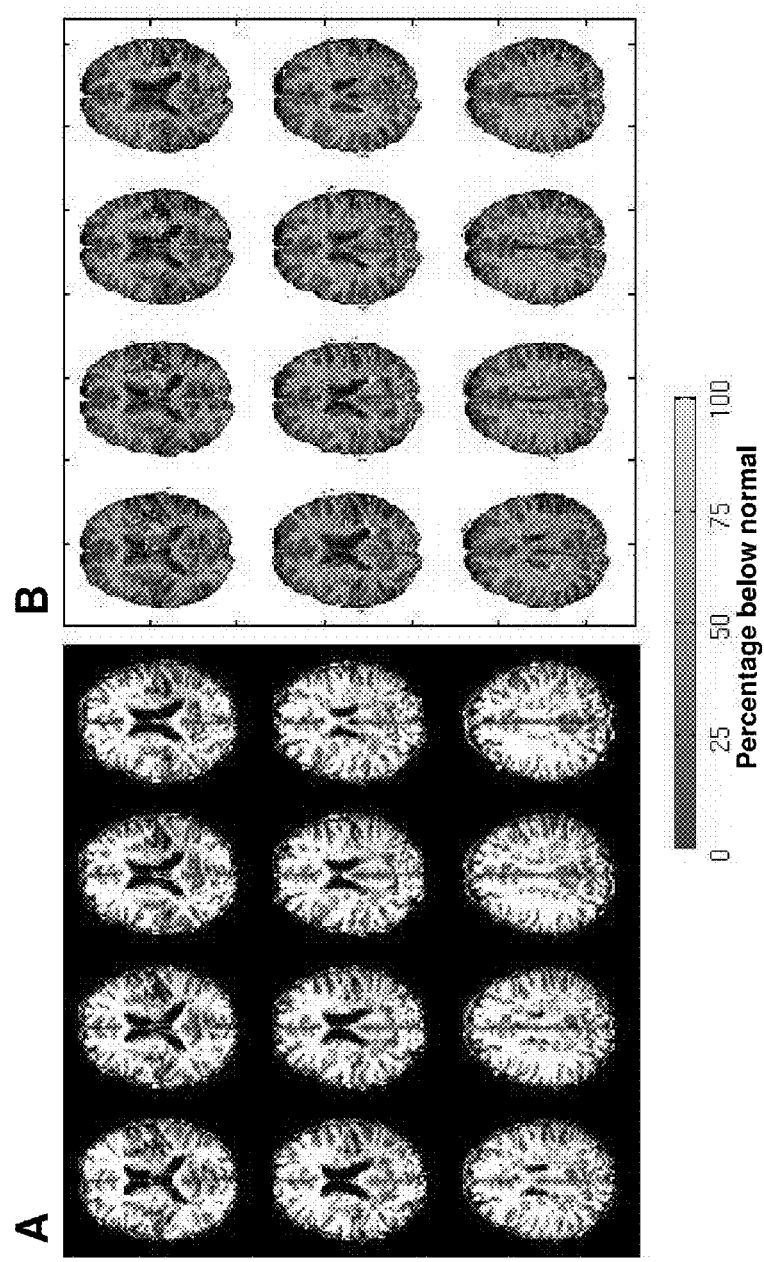
FIG. 8 compares the volume of interacting protons (VIP) and tissue volume (TV) maps of 11 healthy control subjects ("control subjects") and one subject suffering from multiple sclerosis ("MS subject"), as further detailed in Example 3. Panel A shows the VIP map from the MS subject in gray, the color overlay defines the areas that are different from the VIP map from the control subjects (Z>3.5). The color bar defines the percentage value below the norm. Panel B shows the TV map from the MS subject in gray, the color overlay defines the areas that are different from the lipid fraction map from the control subjects.

By aggregating diffusion information across multiple voxels, it is possible to estimate the locations of major white matter tracts (Basser et al., 2000; Mori et al., 1999; Conturo et al., 1999). The diffusion of water within a voxel is influenced by many factors. The cell membrane properties contribute to the diffusion signal, but other factors such as the presence of crossing fibers or overall fiber density also influence the diffusion signal. The heterogeneity of biological factors that drive the diffusion signal limits the interpretation of diffusion measurements (Beaulieu, 2002; Paus, 2010). FIGS. 7 and 8 illustrate the benefit of combining diffusion signals with VIP and TV values as quantitative tissue properties to aid in the interpretation of diffusion measurements,"), as further detailed in Example 3.

Diffusion weighting. Diffusion weighting allows the distinction between rapid and slow diffusion of protons. The brain has three major tissues that magnetic resonance imaging (MRI) can distinguish: gray matter, white matter and cerebrospinal fluid. The gray matter consists of neuronal cell bodies, dendrites, unmyelinated axons, glial cells and capillaries, while the white matter consists mostly of myelinated axons, which transmit signals between different nervous system regions.

White matter can be categorized into different tract groups, i.e. bundles of connecting axons, including projection, association, limbic and commissural tracts as well as tracts in the brainstem. The white matter tracts within a tract group perform similar functions. The projection tract consists of projection fibers that connect the cerebral cortex with the spinal cord, brainstem and thalamus, while association fibers of the association tract interconnect different cerebral cortical areas of the same brain hemisphere. The limbic system plays a key role in high-level mental processes and consists of interconnected gray and white matter structures that form a loop in each brain hemisphere (Mark et al., 1993). The commissural tracts interconnect both hemispheres across the median plane. The cerebrospinal fluid (CSF) fills the space between and around the gray and white matter tissues. Except for cerebrospinal fluid and blood, water molecules are bound in biological systems to other molecules, typically to macromolecules such as polysaccharides and proteins, thereby forming a so-called hydration layer.

The macromolecules in the brain are principally in cell membranes, and in brain white matter about 50% of macromolecules in the brain are contained within the myelin sheaths wrapped around the axons (Norton & Autilio, 1966). Consequently, in the brain white matter the quantitative tissues properties non-tissue volume (TV) and volume of interacting protons (VIP), as a measure of the volume and water surface interaction area of the cell membranes in the brain white matter, depend significantly on the myelin density in each voxel (Milhaud, 2004) and serve directly as a measure of myelin content. The determination of the VIP and, optionally, of the TV, are, therefore, of great diagnostic relevance in detecting disturbances in the myelination process.

Myelination, the establishment of the lipid myelin bilayer around neuronal axons, is essential for normal brain function and normal brain development. The myelin sheath enables the rapid and synchronized information transfer that is necessary for cognitive, emotional and behavioral functions as well as maturation and coordinated movement. Myelin is a large molecule whose function is to insulate the axon of a neuron through the formation of the myelin sheath. Myelinated axons represent the white matter in intracerebral as well as extracerebral areas and are essential for the proper and rapid impulse propagation in the nervous system. When axons lose their myelin sheath (demyelinate), as it happens in cases of demyelination diseases including, but not limited to, multiple sclerosis, acute disseminated encephalomyelitis, chronic inflammatory demyelinating polyneuropathy, Transverse Myelinitis, and the Guillain-Barre Syndrome, signal conduction along the nerves is severely impaired and communication between the brain and other parts of the body becomes disrupted. Since axons cannot be remyelinated, demyelination leads to speech impairment, memory loss, balancing disorders, muscle weakness, neuropathic symptoms such as numbness sensations and cognitive disorders.

2. Methods how to Make and Use the Present Invention

Analysing magnetic resonance images based on quantitative tissue properties such as the non-water tissue volume (TV) and volume of interacting protons (VIP) as a measure of the volume and water surface interaction area of cell membranes and macromolecules in soft tissues and applying these properties in biophysical tissue models, as described by the methods of the present invention, is highly useful in advancing our ability to study neural development quantitatively, to differentiate diseased neuronal tissues from typical, disease-free tissues and to understand the structure and function of key pathways in the human brain.

There is broad interest in deriving quantitative tissue properties using neuroimaging (Tofts, 2003). Quantitative brain tissue properties can be compared across different subjects or from the same subject at different points in time. Such methods are particularly valuable when the quantitative tissue properties facilitate the identification of tissue properties that are significant factors and drivers in a neurological or neurodegenerative disease or disorder.

Methods of the present invention may find application in the prognosis and diagnosis as well as in the therapeutic monitoring of diseases and disorders that relate to improper or insufficient myelination or that display pathological or abnormal characteristics in brain volume or brain white matter connectivity, as evidenced by altered white matter tracts in comparison to healthy controls. These methods may, furthermore, provide a useful tool to detect and assess structure abnormalities and degenerative processes in soft tissues, particularly brain structure abnormalities, to provide a disease prognosis and to monitor disease progression. Specific tissue compartments from which degenerative processes or abnormalities are assessed are, for instance, gray matter, white matter or cerebrospinal fluid volume. Structural abnormalities and degenerative processes include, but are not limited to, changes (decreases or increases) in brain tissue volume and changes in neural connectivity as evidenced by changes in brain white matter tracts/brain signaling pathways affecting signal transmission and information processing.

Neurological disorders and neurodegenerative diseases are debilitating in every aspect of life and gravely diminish its quality. Neurological damage is in most cases irreversible, rendering early diagnosis and continuous, close monitoring of neural abnormalities and degenerative processes absolutely critical for the successful treatment of a subject and for the prevention of more extensive damage. Neural abnormalities and degenerative processes have been found in diseases that affect the central nervous system such as Autism, Schizophrenia, Alzheimer's Disease, but also in metabolic diseases such as type-I and type-II diabetes. Disruptions in brain white and gray matter affect the microstructure of those tissues and impairs brain connectivity.

Autism is a neurological and neurodevelopmental disorder of unknown etiology and so far incompletely understood neuropathology. As described by Schumann and colleagues, the brain in children with autism exhibits a period of early overgrowth in the first three years of life leading to a significantly enlarged brain volume and changed neuroanatomical profile, when compared to healthy controls (Schumann et al., 2010). Brauser reports structural brain changes in children and teenagers suffering from schizophrenia describing lowered brain weight through loss of brain gray matter and enlarged lateral ventricles with increased amounts of cerebrospinal fluid (Brauser, 2012). Diabetes is a metabolic disease with various potential end-organ damages in the body's vascular and nervous systems through chronic hyperglycemia. Considerable loss of brain white and gray matter and disrupted brain white matter tracts were reported in subjects suffering from Type-II diabetes (Chen et al., 2011) and Type-I diabetes (Franc et al., 2011).

Using diffusion tensor imaging and tractography, Gao and colleagues investigated brain white matter changes and abnormal aging in elderly subjects suffering from Alzheimer's Disease (AD) in comparison to healthy elderly subjects as well as healthy young adult subjects. Compared with young adults, brain white matter changes in the anterior part of the brain with a changed myelination pattern were identified in the healthy elderly and the elderly suffering from AD. In addition, a changed myelination pattern was found in the posterior part of the brain of AD subjects (Gao et al., 2011).

Since neural tissue is not accessible for histological evaluation, quantitative, noninvasive imaging methods as those described herein play a key role in the diagnosis and monitoring of the progression of neurological and neurodegenerative disorders and diseases and, in case of therapeutic intervention, for monitoring of therapeutic success.

Methods to Measure Myelin Content in Brain White Matter to Detect Abnormalities or Degenerative Processes Indicative of (i) Demyelination Diseases and Disorders, (ii) Abnormal Brain Development, (iii) Abnormal Aging Process, (iiii) Neurological Disease, (iiiii) Neurodegenerative Disease, or (iiiiii) Metabolic Disease, and Optionally, to Correlate with Cognitive Abilities.

The microstructure of soft tissue such as brain white and gray matter is analyzed using magnetic resonance imaging. The non-water tissue fraction and hydration layer fraction are determined as quantitative tissue properties to quantify the volume and exposed surface area of cell membranes in brain white and gray matter.

Lipid membranes are essential for cellular function, acting both as a selective barrier between the cell interior and its environment and as an interface for cell signaling responses and cell communication. Creating biophysical models that take into account the volume and exposed surface area of cell membranes aids in understanding the membranes' function and physiology.

In embodiments of the present invention biophysical models are utilized to calculate water pools and non-water pools, derived from non-water tissue volume (TV) and volume of interacting protons (VIP). Water pool and non-water pool concentrations are fundamental biological tissue properties that allow quantitative detection of structural abnormalities in soft tissue by comparing water pool and non-water pool concentrations in individual subjects, who, e.g., might suffer from a demyelination or dysmyelination disease, and healthy control subjects. In particular, the comparison of water pool and non-water pool concentrations in individual and control subjects might reveal differences in myelin density and other myelin abnormalities.

Comparing quantitative tissue properties from subjects who possibly suffer from a neurological or neurodegenerative disease with those from healthy control subjects enables the diagnosis of a neurological or neurodegenerative disease. Comparing quantitative tissue properties from the same subject who possibly suffers from a neurological or neurodegenerative disease over a defined period of time enables the monitoring of disease progression and disease outlook/prognosis. Comparing quantitative tissue properties from the same subject who possibly suffers from a neurological or neurodegenerative disease and who has started treatment to address such neurological or neurodegenerative disease over a defined period of time enables the monitoring of therapeutic success. The methods of the present invention have already been successfully used to measure differences in the myelin content in different regions within the corpus callosum, which is part of the white matter in brain and lies beneath the cortex. Differences in myelin content may be used to stratify subjects who suffer from demyelination diseases such as multiple sclerosis or dysmyelination disorders, to prognose disease and to monitor disease progression.

White matter abnormalities, as observed in demyelination as well as dysmyelination diseases and disorders, can occur intracerebrally and extracerebrally. Intracerebral white matter includes the various regions of the corpus callosum, while the optical nerve and the spinal cord are examples of extracerebral white matter. Diseases and disorders that involve gradual loss or flawed production of the myelin sheath can be classified into primary demyelination, secondary demyelination and dysmyelination. In the case of primary demyelinating diseases, normally formed myelin around the axons is destructed, but the axons themselves remain mostly intact.

Multiple sclerosis is probably the most well-known primary demyelinating diseases; it is currently considered an auto-immune disorder, where a subject's own immune cells attack the nervous system, cause inflammation and subsequently demyelination of the neurons. When substantial amounts of myelin are destructed, the neurons can no longer effectively conduct electrical signals. Multiple sclerosis lesions commonly involve white matter areas inside the brain (cerebellum) and outside the brain, in particular the spinal cord and the optical nerve.

The quantitative identification of white matter abnormalities in the brain and other soft tissues might provide a prognostic indication of the progression of multiple sclerosis in the years to come. Multiple sclerosis has been found to cause distinct lesions within the spinal cord (Bot et al., 2004). The early detection of spinal cord lesions and injuries might provide an indication of developing locomotor disabilities, either in the context of multiple sclerosis where gradual demyelination can lead to chronic lesions in the spinal cord or in the context of central inflammatory disorders that can lead to asymptomatic, subacute or acute lesions in the spinal cord.

Methods of the present invention might also be useful for correlating gray and white matter abnormalities with cognitive ability observations in subjects who are suspected or confirmed of suffering from a white and gray matter disease. Such observations focus particularly on cognitive abilities such as reading or writing abilities, but also include behaviors such as anxiety, depression, paranoia, dementia, delirium, confusion, hallucinations and mania, all assessed according to standard procedures in the neuroscience field.

Methods of the present invention might also find application in segmenting the brain in its three components, white matter, gray matter and cerebrospinal fluid.

Methods of the present invention might also be useful for identifying pharmacological agents that modulate myelin content in neuronal tissue of a non-human model and that might be efficacious for treating demyelination diseases. Following exposure of a non-human model organism to a pharmacological agent that might act as a modulator of myelin content in white matter by slowing down or stopping demyelination processes in case of a demyelination disease, certain soft tissue parts of the non-human model organism can be imaged using MRI and water pool and non-water pool concentrations can be calculated and compared during the course of several, consecutive measurements that might span over days, weeks or months. The methods of the present invention would allow the quantitative detection of myelination changes in the non-human model organism due to the action of the pharmacological agent by comparing differences in myelin content with measurements in the absence of the pharmacological agent, identifying the pharmacological agent as a modulator of myelin content in white matter if the myelin content in the presence of the pharmacological agent relative to the myelin content in the absence of the pharmacological agent is higher.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

EXPERIMENTAL PROCEDURES

The following methods were used in the examples that are described further below. The methods and examples described in the following are similar to the methods and examples observed in preliminary studies and described in the U.S. Provisional Application No. 61/437,587, filed Jan. 28, 2011, which is incorporated herein. The previously used terms "tissue fraction" and "TF" were replaced herein by "tissue volume" and "TV"; furthermore, the previously used terms "hydration layer fraction" and "HLF" were replaced herein by "volume of interacting protons" and "VIP".

MRI Acquisition.

Human subjects: Measurements were performed on sixteen healthy human adult subjects. In addition, 10 volunteers with relapsing remitting multiple sclerosis (diagnosed based on revised McDonald's Criteria (Polman et al., 2005) were recruited from the Stanford Neuroimmunology Clinic. The disease duration was 2-17 years with Expanded Disability Status scale <3.0 (Kurtzke 1983). All patients were on disease modifying treatments (2 natalizumab, 1 glatiramer acetate, 7 interferon beta-1a) and free of steroids for at least 3 months at the time of MR imaging.

Data were obtained from five MR scanners: a 0.5 T GE Signa SP (N=2), two different 1.5 T GE Signa MRI scanners (N=4) and two different 3 T GE Signa (N=26). At 0.5 T, we used the quadrature head coil. At 1.5 T, we used two different 8-channel receive-only head coils. At 3 T, in one magnet we used an 8-channel receive-only head coil and in another we used a 32-channel receive-only head coil.

The quantitative VIP and TV parameters were measured from Spoiled gradient recalled echo (SPGR) images acquired with different flip angles ($\alpha=4°$, $10°$, $20°$, $30°$, TR=20 ms, TE=2 ms). The scan resolutions at different field strengths were: 0.5 T, 1.5×1.5×3 mm; 1.5 T, 1.5 mm$^3$; 3 T, 0.9375× 0.9375×1 mm$^3$.

For T1 calibration, all subjects measured at 1.5 T and 3 T were also scanned using spin echo inversion recovery with an EPI read-out (SEIR-epi). The scan was done with a with a slab inversion pulse. For SEIR-epi the TR was 3 sec at 3 T and 2.5 sec at 1.5 T. The echo time was TE minimum full; inversion times were 50, 400, 1200, 2400 msec. We used 2 mm² inplane resolution and slice thickness 4 mm. The EPI readout was performed using 2× acceleration in 3 T and no acceleration in 1.5 T.

For comparison, several subjects in the 1.5 T scan also participated in other MR imaging measures. Several of the subjects participated in magnetization transfer measurements that are described in detail elsewhere (Stikov et al., 2011). To use the pre-scan calibration data we made sure that the manufacturer's pre-scan was performed only for the first flip angle scan and these parameters were used for the remaining scans. The MS subjects (N=10) participated in fluid attenuated inversion recovery (FLAIR) scan from each of the MS patients.

Lipid phantoms. Data were obtained using a 1.5 T GE Signa MRI scanner. SPGR images were obtained using parameters similar to those used with human subjects (see above). The data processing was identical to the human processing with two exceptions. The coil biases were estimated by a single set of 3D $2^{nd}$ order polynomial approximate over homogenous region (the vessel was filled with PBS). The receive-coil inhomogeneity correction was scaled so that the water volume (WV) of the PBS region was 1. The transmit-coil inhomogeneity correction was scaled so that the T1 of the PBS region was equal to the T1 of water at room temperature.

SPGR imaging is particularly useful in brain imaging to achieve T1 weighted images. The current application uses short TE and at list 2 flip angle ($\alpha$) between 4 to 4°-30°. The RF excite is done with epi SEIR.

T1 mapping and transmit-coil inhomogeneity correction: In a perfectly calibrated system, measuring with multiple flip angles enables us to compute both T1 and $M_0$ (see Equation 1.1). In practice the transmit-coil imperfections scale the flip angle parameter across the volume and produce erroneous T1 and $M_0$ estimates.

$$S(\alpha) = M_0 \sin(\alpha) \left( \frac{1 - e^{\frac{-TR}{T1}}}{1 - \cos(\alpha) e^{\frac{-TR}{T1}}} \right) \quad 1.1$$

Our strategy to overcome the transmit-coil calibration errors is as follows. We first use SEIR-epi to measure an unbiased, low resolution, T1 map of the whole brain. We calculate T1 from SEIR data using the method described by Barel et al. (Banal et al., 2010). We then align the T1 data with a matched, low-resolution representation of the SPGR data. From the T1 and several flip-angle SPGR values, we use a nonlinear least-squares (NLS) solver and estimate the transmit-coil inhomogeneity and $M_0$ (Equation 1.1). Next we interpolate the low-resolution transmit-coil inhomogeneity data to the resolution of the original SPGR measurements. We assume that the transmit-coil inhomogeneities are smooth and can be estimate by local regressions of hyper-planes (3D). We derive the hyper-planes coefficients using the whole-brain data, although we exclude certain voxels that are likely to be outliers. First, we exclude voxels with a T1 value lower than 2 sec (Barral et al., 2010). Second, we exclude voxels with transmit coil inhomogeneity values more than 2 standard deviations from the mean transmit-coil values. Using the fitted polynomial, we interpolate the transmit-coil inhomogeneity estimates to the high-resolution SPGR. Regions in the high-resolution SPGR that are not covered by the low-resolution bias map are estimated by a $2^{nd}$ order polynomial that spans the bias volume. We use the estimated transmit-coil inhomogeneity and several flip-angle SPGR measurements to derive the high-resolution T1 and $M_0$ maps. These were calculated using a nonlinear least-squares (NLS) fitting procedure (Chang et al. 2008) to minimize the difference between the data and the signal equation predictions (Equation 1.1).

T1 data acquired at 0.5 T used a combined transmit-receive quadrature head coil. The coil correction applied to the data in 1.5 T and 3 T is not applicable for this field strength. In this case we assume that the transmit coil gain was minimal due to the low field strength. These data were used only for comparison of T1 values in different strength.

Proton density mapping-receive coil inhomogeneity-correction. At each point in the volume, proton density ($\rho$) is proportional to $M_0$. But the $M_0$ data are contaminated $T_2^*$ decay and receive-coil imperfections and (see Equation 1.2). For short TE measurements, the $T_2^*$ decay can be neglected. Hence, the main challenge is to remove the receive-coil inhomogeneity. We estimated the receive coil inhomogeneity by combining data obtained in the individual coils. Just as in parallel imaging algorithms, the estimation procedure relies on the fact that multiple coils measure the same $\rho$ but with different coil gains. The estimation algorithm follows. The brain image was gridded into a set of partially overlapped volumes each about ~20 mm³ and with 50% overlap with its neighboring volumes. The volumes are processed independently. For $i^{th}$ coil we estimate $M_{0,i}(\alpha)$ from the signal $S_i(\alpha)$ and T1 map and corrected $\alpha$ (above) using Equation 1.1

$$M_{0,i}(\alpha) = \frac{S_i(\alpha)\left(1 - \cos(\alpha) e^{\frac{-TR}{T1}}\right)}{\sin(\alpha)\left(1 - e^{\frac{-TR}{T1}}\right)}$$

We used the average of these estimates over $\alpha$ as the mean $M_{0,i}$ that volume and coil. We assumed that within each volume the gain $g_i$ is a $2^{nd}$ order polynomial spanning the volume (Notestedamus et al., 2009). The fitting procedure is constrained to assume that all $M_{0,i}$ share the same $\rho$ component. From $g_i$ and $M_{0,i}$, each coil estimates a $\rho_i$ (Equation 1.2). We solve for the polynomials $g_i$ that produce the greatest agreement between the $\rho_i$ estimates from the different coils $$\min_{g_i}\left\{\sum (\rho_i - \bar{\rho})^2\right\}.$$

To regularize the search across the polynomial coefficients we further require that the correlations between the $g_i$ does not exceed the correlations between $M_{0,i}$ and $g_i > 0$. The last step is to combine the $\bar{\rho}$ maps estimated from each volume. We set the mean in overlapping blocks to be equal and then average the measures across blocks.

Volume Calculation: Tissue and Water Volumes (TV and WV):

We derive the water and the tissue volume (WV and TV) in each voxel from the $\rho$ map. We use the calculated $\rho$ values in CSF as a baseline to indicate a voxel with only water. Hence, to derive the fraction of the voxel volume that is water we normalize the $\rho$ map by the mean value from a region of interest (ROI) in the cerebrospinal fluid (CSF). The CSF is identified by the FreeSurfer segmentation (Fischl and Dale, 2000) and is limited to voxels with a T1 in the range 4-5 s (Hopkins et al., 1986). Aside from water, the molecules present in CSF are in relatively low concentration, so the assumption that the normalized ρ measures water fraction is reasonable. The normalized ρ values are between 0 and 1, and the few locations greater than 1 are clipped. These normalized ρ maps measure water volume fraction (WVF) in each voxel. The tissue volume fraction is just 1−WVF and both can be expressed in volume units when we multiply the fraction by the voxel volume.

Reliability of Map Estimates

Humans

To measure the T1 estimation error, one of the subjects was scanned 12 times with a large set of flip angles (α= [4°10°20°30°30°20°10°4°10°20°30°4°20°4°10°30°]) and 2 mm³ voxel size, but the same TR and TE values in 1.5 T magnet. We performed a bootstrap analysis of these scans, randomly selecting a set of flip angles=[4°10°20°30°] in a thousand repeats to estimate the T1 map using a linear approximation (Fram et al. 1987). The T1 estimation error was defined as the standard deviation of the estimated T1 values.

To further characterize the effect of flip angles, the same subject was scanned with slightly different flip angles [3°5°9°11°18°22°26°34°]. The T1 value was estimated again with a set of values higher [5°11°22°34°] and lower [3°9°18°26°] than the standard flip angle set. The estimated T1 values from these two sets were compared to the T1 values derived from the standard flip angle set. In addition one subject were also scanned with two sets of flip angles =[4°10°20°30°] and [4°4°18°18°].

To characterize the effects of TR and TE on the estimation, another subject was scanned using TR=[20, 80] ms; TE=[2, 12] ms; α=[4°, 18°]; voxel size=2 mm³ at the 1.5 T magnet.

To estimate the reliability and generalization of the maps in human subjects, we performed multiple scans on different scanners using the parameters listed above. To estimate reliability within instruments, two subjects had three measurements in the same 1.5 T scanner and two subjects were scanned twice in the same 3 T scanner with different receive coils.

To estimate reliability across instruments two subjects had two measurements in two different 1.5 T, and two subjects had two measurements in two different 3 T scanners. Three of the subjects scanned in the 1.5 T scanner were also scanned in a 3 T scanner. We also checked the repeatability using different parameters.

Phantoms

A homogenous agar phantom was used to evaluate the quality of the RF-coil inhomogeneity correction. To estimate the RF-excite homogeneity we measured the SEIR-epi and T1. We compared the phantom T1 map using SEIR-epi with a gold standard SEIR (Barral et al., 2010).

To evaluate the receive homogeneity correction we measured the ρ value in the homogenous phantom. The standard deviation of the ρ value measures the reliability of the coil receive measurements.

Related Methods for Applications

T1 estimate with spin-echo inversion recovery (gold standard). Three slices were acquired using the SE-IR sequence, a birdcage head coil receive-only, and the following parameters: TR=2550 ms, TE=10 ms, TI=[50, 400, 1100, 2500] ms, BW=±32 kHz, FOV=24×18 cm², slice thickness=5 mm (Banal et al., 2010).

Data Alignment

We collected high-resolution T1-weighted anatomical images for each subject using an 8-minute sagittal 3D-SPGR sequence (1 mm³ voxel size). Several anatomical landmarks were manually defined in the T1 images: the anterior commissure (AC), the posterior commissure (PC), and the mid-sagittal plane. With these landmarks, we used a rigid-body transform to convert the T1-weighted images to the conventional AC-PC aligned space. This T1-weighted image was used as a common reference for alignment of the T1, PD, MT and DTI maps. To compare data across multiple subjects, the raw images were (1) aligned to a T1-weighted reference image (MNI152) using a rigid-body mutual-information algorithm and (2) resampled to 2 mm isotropic voxels using a 7th-order b-spline algorithm based on code from SPM5 (Friston & Ashburner, 2004).

Magnetization Transfer Measurements

For five of the subjects the T1 mapping procedure was followed by magnetization transfer SPGR scans with variable offset frequency (TR=32 ms, TE=2.4 ms, α=10°, Δ=[3, 6, 9, 12] kHz) (Yarnykh & Yuan, 2004).

Diffusion Tensor Imaging (DTI) and Tractography

The whole-brain DTI measurements were performed using a diffusion weighted spin-echo EPI sequence with isotropic 2 mm³ resolution. We measured 80 diffusion directions (40 non-colinear) with a b-value of 0.9 ms/μm² and seven repeats of the same sequence with no diffusion weighting. Fiber tracts were estimated using a deterministic streamlines tracking algorithm (Basser et al, 2000; Mori et al., 1999). The methods are described in detail elsewhere (Stikov et al., 2011; Dougherty et al., 2005). The white matter tract were identified in each individual by restricting fibers to two way-point regions of interest (ROIs) that were defined based on a DTI atlas of human white matter (Wakana et al., 2004).

For both fiber tracts of interest in this study, tractography algorithms estimate a dense set of core pathways along with a small proportion of pathways that are outliers. To minimize the influence of the outliers we combined data from different voxels in a weighted fashion, assigning greater weight to voxels near the core of the estimated tract (Corouge et al., 2004).

The algorithm for calculating the weights is the following. All fibers were clipped to the portion spanning between the two way-point ROIs such that each fiber was approximately the same length. Then the fiber groups were resampled to equal numbers of nodes; in this case we used 50 nodes for each tracks. We computed the mean position of each of the 50 nodes, and defined this as the fiber tract core. We specified the diffusion at each node of the fiber group core as a weighted average of the diffusion measured near the equivalent node of each individual fiber in the group. The contribution of a given fiber is weighted by its distance from the tract core. We measured the distance from the node to a voxel using the covariance matrix of the node position. Specifically, if a voxel position is X, the mean position is $X_0$, and the covariance matrix of the 3D node position is C, then we calculate the Mahalanobis distance, d, as:

$$d = \sqrt{(X-X_0)^t C^{-1} (X-X_0)} \qquad 1.8$$

The weight assigned to data from a voxel is the inverse of its distance, d. This procedure assigns higher weights to fibers near the bundle core.

The VIP and TV Theory

The SPGR signal equation (equation 1.1) depends on three tissue related MR constants, T1, $T_2^*$ relaxation times and proton density (ρ). The equation also depends on acquisition parameters TR, TE flip-angle (α) and coil inhomogeneity.

$$S(\alpha) = M_0 \sin(\alpha) \left( \frac{1 - e^{\frac{-TR}{T1}}}{1 - \cos(\alpha)e^{\frac{-TR}{T1}}} \right) \quad 1.1$$

The $M_0$ term combines g, a scale factor that characterizes receive-coil inhomogeneity, the proton density (ρ), and $T_2^*$ decay constant (equation 1.2).

$$M_0 = g\rho e^{\frac{-TE}{T2}} \approx g\rho \quad 1.2$$

For the short TE measurements in this work (~2 ms), the $T_2^*$ decay can be neglected and thus $M_0 \approx g\rho$. In principle, T1 and $M_0$ can be estimated by collecting measurements with at least two flip angles. In practice the receive coil and the transmit coil are not perfectly calibrated. The receive-coil imperfection influences only $M_0$. On the other hand, the transmit-coil imperfection means we do not accurately know α at each brain voxel, and this produces erroneous estimates of both T1 and $M_0$. Consequently, we must estimate both transmit and receive coil inhomogeneity (see Methods) to derive the T1 and ρ maps accurately.

The values ρ and T1 measure different tissue properties. The proton density map values, ρ, are proportional to the amount of water in each voxel. We assume that voxels in the CSF are entirely filled with water, so the water fraction (WVF) is the ratio of the ρ-value in a voxel to the ρ-value in CSF. The non-water fraction, 1−WVF, contains membranes and macromolecules. We refer to this as the tissue volume fraction, TVF=1−WVF. Multiplying TVF (or WVF) by the voxel volume converts TVF to the tissue volume, TV.

Biophysical theory explains T1 relaxation time in brain tissue as arising from at least two distinct mechanisms, free water protons and protons that interact with the surface of local macromolecules (Mansfield and Morris 1982; Bottomley et al., 1984; Rooney et al., 2007). The water protons in the free pool exchange their energy with the surroundings (lattice) relatively infrequently. Changes in the mean field do not have a significant impact on their $T1_f$ value (Bloembergen et al., 1948). The protons bordering the macromolecules have a higher probability of T1 relaxation with the lattice, and these protons convert to the lower energy state more rapidly than the free water protons ($T1_c \ll T1_f$). The mechanisms for T1 reduction near macromolecules is still an active research field and mechanisms like dipole interaction, proton or molecule exchange, magnetization transfer as well as slow diffusing hydration water pools have been suggested. The $T1_b$ value depends on the mean field (Bloembergen et al. 1948; Nelson & Tung, 1987). For a review of the theory at this fine scale see (Caluccia & Caluccia, 2009; Halle, 2006).

Several groups have shown that the observed T1 in brain tissue follows a simple exponential decay, and the T1 value depends on field strength (Bottomley et al., 1984; Rooney et al., 2007). This is surprising because the lattice is not comprised of a single type of tissue. This can be explained by the analysis of T1 values in substances comprising multiple tissue compartments. Zimmerman (Zimmerman et al. 1957) showed that when there is a fast exchange of protons between compartments, the relaxation of the entire sample is a single exponential with a time constant equal to the weighted ($C_i$) sum of each individual compartment's time constant $$\left( \frac{1}{T_{c,i}} \right).$$

$$\frac{1}{T1} = \sum_{i=1}^{n} C_i \frac{1}{T1_{c,i}} + \left(1 - \sum_{i=1}^{n} C_i\right) \frac{1}{T1_f} \quad 1.4$$

The protons bordering the macromolecules interact with different proteins, lipids surfaces and paramagnetic ions, each may have its own T1 value $T1_{c,i}$. These values tend to be significantly shorter than $T1_f$ and thus the T1 of each voxel is significantly influenced by the T1 in these compartments. We aim to characterize the volume of these interacting protons (VIPs). If we define $T1_C$ as $$\frac{1}{T1_C} = \sum_i C_i \frac{1}{T1_{c,i}} \bigg/ \left(\sum_i C_i\right) \quad 1.5$$

We can rearrange the terms $$\left(\sum_i C_i\right) \frac{1}{T1_C} = \sum_i C_i \frac{1}{T1_{c,i}} \quad 1.6$$

We define the sum of the concentrations as the fraction of these water interacting protons (WIPs) and re-write Equation 1.4 as $$\frac{1}{T1} = WIP \frac{1}{T1_C} + (1 - WIP) \frac{1}{T1_f} \quad 1.7$$

We can rearrange Equation 1.7

$$WIP = \frac{\left(\frac{1}{T1} - \frac{1}{T1_f}\right)}{\left(\frac{1}{T1_C} - \frac{1}{T1_f}\right)} \quad 1.8$$

To estimate the volume of interacting protons VIP in a voxel, we multiply WIP by the fraction of water in the voxel (WVF=1−TVF) and the voxel volume, V $$VIP = WIP (1-TVF) V \quad 1.9$$

Hence, we can estimate VIP from the measurements T1 and PD and the values $T1_f$ and $T1_C$ (Equations 1.8, 1.9). The free pool $T1_f$ can be theoretically estimated (BBF (Bloembergen et al., 1948)) and has been measured to be $T1_f \sim 4.5$ sec in body temperature in the human brain CSF (Hopkins et al., 1986). The open question is how to estimate $T1_C$.

Fullerton et al. (Fullerton et al., 1984) provide an insight into the value of $T1_C$, which is a summary of the T1 values in the tissue compartments. They measured a wide range of biological tissue in vitro after pumping out the free water. They found that for magnetic field strengths between 5 MHz-100 MHz the $T1_C$ values depend linearly on the Larmor frequency (L, MHz)

$$T1_C = \alpha_1 L + \alpha_2 \quad 1.10$$

We can estimate this relationship in vivo using the following method. We can measure T1(L) of a subject with N brain voxels at two magnetic field strengths; this yields 2N measurements. There is one unknown VIP value for each voxel, and two unknown values $\alpha_i$ for the entire data set. With N+2 unknowns and 2N measurements, we can estimate the parameters $\alpha_i$ within the range of measured field strengths. In the Results section we show that for field strengths between 0.5 T and 3 T the data are well-fit using the formula $$T1_C = (0.632L + 104.2) \times 10^{-3} \quad 1.11$$

The $T1_C$ parameter has units of seconds and L is specified in MHz. The parameter represents the mean T1 relaxation of the human white matter tissue compartments. This is the mean value we expect to find if we extract the human white matter, pump out the water, and measure T1 as a function of field strength at body temperature.

We can assemble the equations into a single unified expression that estimates the apparent volume of interacting protons assuming that T1 in the tissue compartment equals $T1_C$ $$VIP = \frac{\left(\frac{1}{T1(L)} - \frac{1}{T1_f}\right)}{\left(\frac{1}{T1_C(L)} - \frac{1}{T1_f}\right)} \times (1 - TVF) \times V \quad 1.12a$$

Or including the specific parameters $$VIP = \frac{\left(\frac{1}{T1(L)} - \frac{1}{4.5}\right)}{\left(\frac{10^3}{0.632L + 104.2} - \frac{1}{4.5}\right)} \times (1 - TVF) \times V \quad 1.12b$$

The VIP value has several properties that make it a useful complement to T1 or T1-weighted measurements for brain research and clinical assessment. The VIP units are simply volume and thus they are independent of field strength (over the range of 0.5 T-3 T); in contrast, T1 or T1-weighted values depend on field strength.

An intuition concerning the physical meaning of VIP is this: After excitation, the excited water protons give up their energy to the lattice. The VIP measures the volume of excited protons that relax by interacting with the tissue (lattice). Thus, the VIP depends on the tissue volume as well as the efficiency with which the protons and tissue interact to shorten the relaxation time.

This suggests that another interesting measure is the ratio VIP/TV. This ratio normalizes the volume of interacting protons per unit tissue volume, which is useful for interpreting how efficiently the protons and tissue interact. The ratio estimates for a given tissue volume how much the $T1_C$ value in a voxel differs from the mean $T1_C$ value. This ratio may detect tissue property changes accounting properly for tissue volume.

There are several key assumptions to this model. First, the fast exchange assumption (Zimmerman et. al. 1957) (Equation 1.4) may not model correctly the interactions between distinct tissue pools; in the case of slow exchange the rule of combination between multiple pools differs from the one in the current model. Second, the linear dependence of all the compartments, $T1_C$ on magnetic field is an approximation (Equation 1.10). The nuclear magnetic resonance theory and measurements suggest that the relationship is nonlinear over a large range but approximately linear in the restricted range from 0.5 T to 3 T (Bloembergen et al., 1948; Mansfield & Morris, 1982; Fullerton et al. 1984).

Even if these limitations exist at the nanometer scale, it is still plausible that the first-order model of VIP and TV is a useful approximation for human neuroimaging data acquired at the millimeter scale. We further performed a series of experimental measures that evaluate how reliable the VIP and TV values are, and how well they serve in interpreting human neuroimaging measurements of white matter tissue properties.

The following examples are put forth so as to provide those of ordinary skill in the art with a complete disclosure and description of how to make and use the present invention; they are not intended to limit the scope of what the inventors regard as their invention.

EXAMPLE 1

Deriving the Volume of Interacting Protons (VIP) and Tissue Volume (TV) from T1 and Proton Density (pd) Maps as a Measure of Tissue Content The non-water tissue volume (TV) and volume of interacting protons (VIP) are estimated by combining two fundamental magnetic resonance maps: T1 and proton density. As described in the theory section above, the estimation is based on the nuclear magnetic resonance theory for T1 (Bottomley et al., 1984; Mansfield & Morris, 1982; Bloembergen et al., 1948). Accordingly, the estimation of T1 (which is in units of seconds) can be transformed into units of volume. In the below described study, we tested the accuracy of our biophysical model and implementation by estimating VIP and TV values from the same brain regions in instruments with field strengths ranging from 0.5 Tesla (T) to 1.5 T and 3 T using a variety of RF coils. The agreement of the VIP measurements across these conditions supports the accuracy of our biophysical model and the RF bias correction techniques. The measurement provides a valuable option to noninvasively measure membrane and macromolecule content throughout various brain regions.

Lipid Phantom Measurements

We describe neuroimaging methods to estimate the tissue volume (TV) of membrane and macromolecules and the (apparent) volume of interacting protons (VIP), that is, the volume of the protons that interact with the membrane and macromolecule surfaces (FIG. 1). The macromolecules in the brain are principally in cell membranes and proteins. In the white matter about 50% of the macromolecules are contained within the myelin sheaths wrapping the axons (Norton et. al. 1966). Hence, in the brain's white matter the TV and VIP values depend significantly on the myelin density in each voxel.

Figure 2:
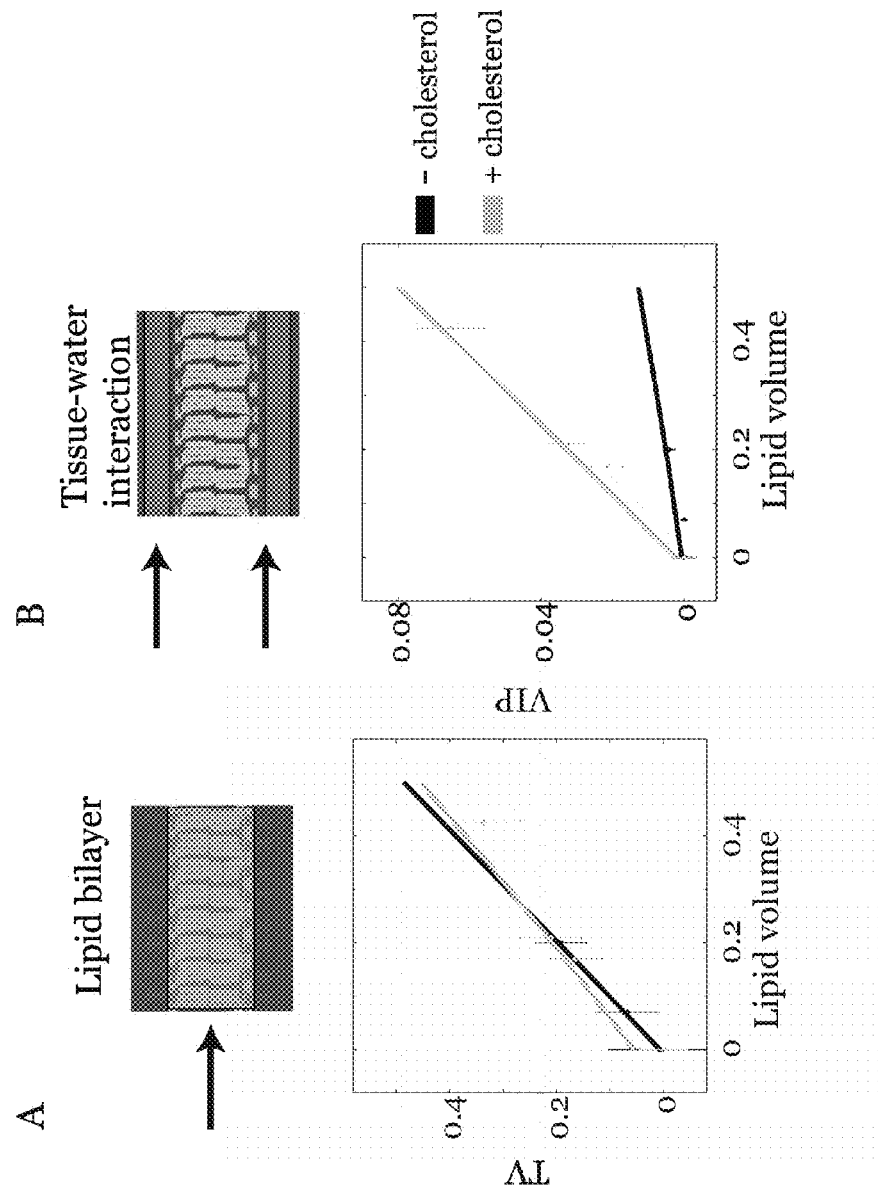
FIG. 2 shows tissue volume (TV) and volume of interacting protons (VIP) maps with lipid phantoms, as further detailed in Example 1. Panel A shows that the TV estimation reliably quantifies the volume (with a standard deviation (STD) 0.065) of two lipid mixtures. The TV estimation is effected from both uncorrected transmit and receive inhomogeneities. The fact that the TV estimation is correct confirms that the inhomogeneities can be estimated. Panel B shows the VIP values. Both mixtures show a gradual increase with respect to the lipids volume, but at a different rate. Hence the VIP is sensitive not only to the macromolecules' concentration, but also to their content.

In the initial experiments we estimated TV and VIP in phantoms with controlled volumes and surface properties. We constructed PC lipid mixtures with and without cholesterol in the lipid membrane. Each type of mixture was made using three lipid volume levels (see Methods). The TV reliably quantified the lipid volume for both membrane types, i.e., lipid with and without cholesterol (FIG. 2A). The raw measurements are influenced by both transmit and receive inhomogeneities, so the accurate TV estimates show that these inhomogeneities can be corrected for these tissue samples. For both mixtures, the apparent VIP increased with lipid volume, as illustrated in FIG. 2B.

Unlike TV, the VIP depends on the cholesterol content of the lipid membrane. The cholesterol content changes the slope of the dependence between VIP and lipid volume. This agrees with earlier work showing that different macromolecules (ref) and in particular cholesterol (ref) change the ability of the surface to reduce T1 and therefore VIP estimation. It is also in agreement with the idea that the apparent VIP summarizes both surface concentration and reactivity.

Given that the TV estimate is independent of the vesicle cholesterol content, we used the TV measurement to normalize the VIP measurement. The ratio of these two quantities is a measure of the average surface reactivity.

Modeling Field Strength Dependence

Figure 3:
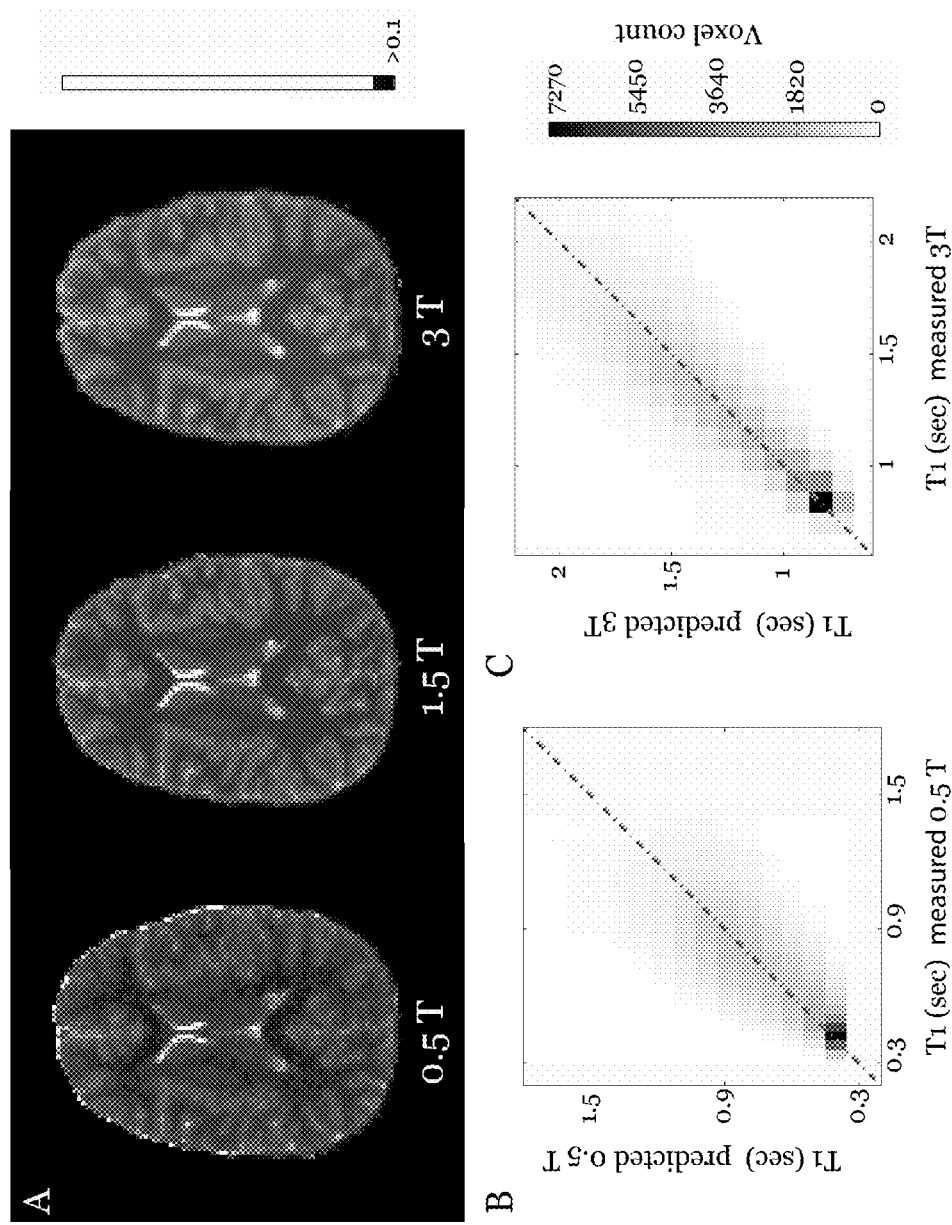
FIG. 3 illustrates the T1 dependence on field strength, as further detailed in Example 1. Panel A shows the T1 map of the same subject in three different field strength 0.5 Tesla (T), 1.5 T and 3 T. Panel B shows that T1 in 0.5 T can be predicted from the T1 in 1.5 T with an R ~0.53. Panel C shows that T1 in 3 T can be predicted by T1 in 1.5 T with an R=~0.73.

T1-values depend on the mean field (B0) level Bottomley et al., 1984; Rooney et al., 2007). The three images in FIG. 3A show the increase in T1 levels measured in identical brain slices at three B0 levels (0.5 T, 1.5 T and 3 T). In the Theory section, we modeled the T1 value as depending on two terms. The first is a contribution from the protons adjacent to macromolecules, $T1_c$, which varies linearly with field strength over a modest range (0.5-3 T). The second is a contribution from the free water, $T1_f$ which is field strength independent.

To predict how T1 varies with field strength requires calculating the linear coefficients relating $T1_c$ to field strength (Equation 1.10). We estimated the coefficients by choosing 100 voxels randomly from the white matter and fitting the 200 T1 measurements with the two parameters in Equation 1.10 and 100 WIP parameters (Equation 1.7). We repeated the fitting with 1500 samples and calculated the mean and standard deviation of the two linear model coefficients in Equation 1.11. The estimated coefficients are $a_1$=0.632±0.028 and $a_2$=104.2±1.7.

To validate the theory and the measurement procedure, we predicted T1 measurements across field strength. We used data from two field strengths (1.5 T and 3.0 T) to estimate the linear coefficients. We then used the 1.5 T data to predict an independent data set obtained at 0.5 T data (FIG. 3B). We then collected yet another independent data set at 1.5 T and 3 T on a third subject. Using the parameters from the first two subjects, we used the 1.5 T data to predict the 3 T data (FIG. 3C). The corresponding correlation between the measurements and predicted values are R=0.53 and R~0.9.

Deriving Tissue Properties TV and VIP

The accuracy of the T1 model predictions supports the theory and shows that we can derive a scanner-independent biophysical parameter: the apparent VIP within each voxel (Equation 1.12b).

The VIP depends on two terms (Equation 1.9): one term is the amount of water interacting with the surface of macromolecules and membranes (WIP), and the second term is the amount of tissue (TV). These tissue properties are independent of the instrument.

Figure 4:
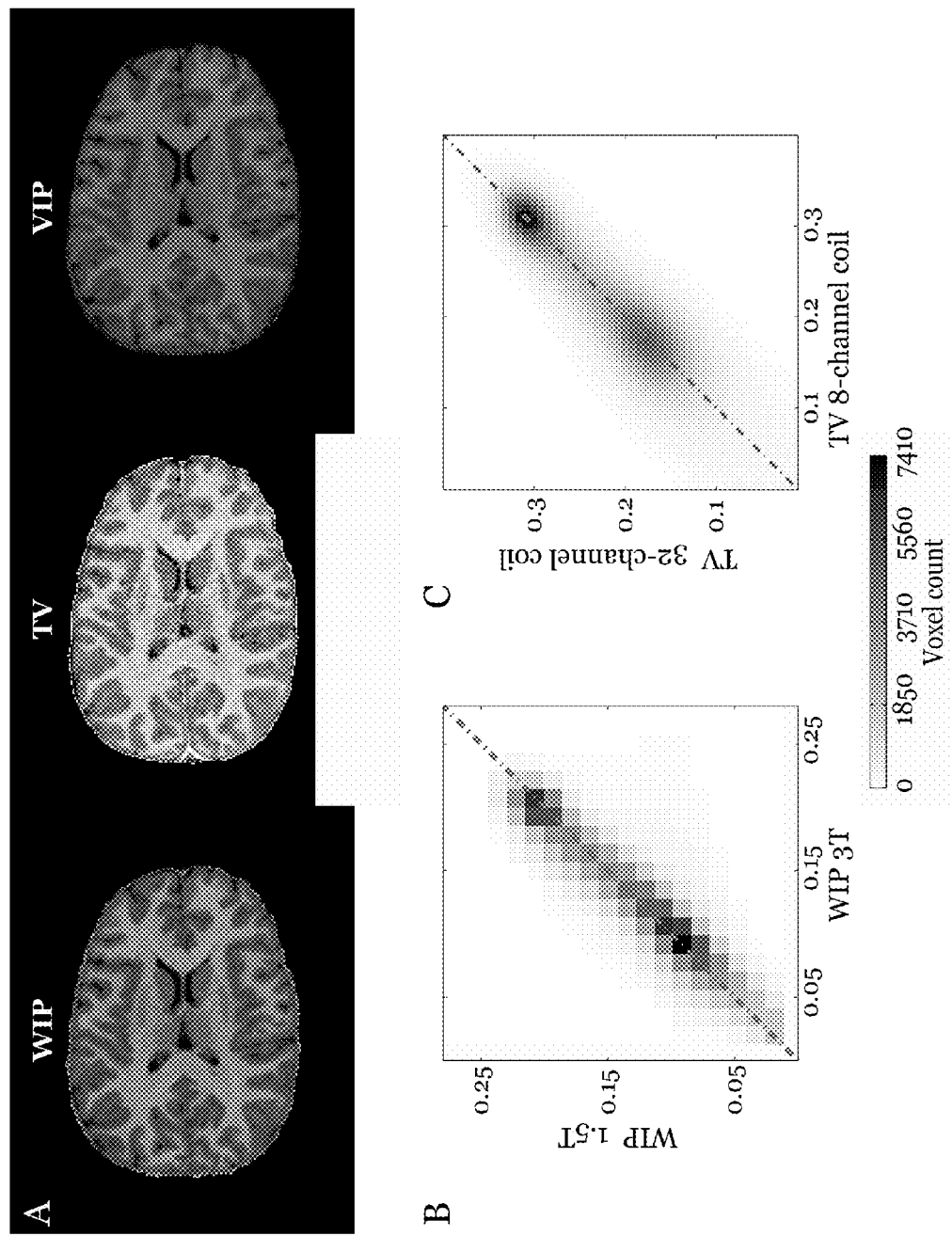
FIG. 4 shows that volume of interacting protons (VIP) and tissue volume (TV) are independent of magnetic field strength and coils, as further detailed in Example 1. Panel A shows axial sections obtained of the VIP as well as the volume of interacting protons in the water (WIP) map and the TV map. The units used for the maps are ml (for 1 ml voxel). The maps are corrected for RF-coil inhomogeneities, as described in the experimental methods. Panel B shows a scatterplot of WIP at two field strength levels. Panel C shows TV with two different coils (8 and 32).

We evaluated the instrument independence of the tissue property estimates, as illustrated in FIG. 4. Panel A shows the three tissue property maps: WIP, TV and VIP. Panel B compares estimates of WIP obtained at different field strengths. Panel C compares estimates of TV using different coils at 3 T. The consistency of the estimates across field strengths and coils supports the analysis and suggests that the Theory interprets the MR parameters correctly and that the methods for removing coil bias derive tissue properties accurately. See below for additional measures of reliability.

The TV and VIP values differ between parts of the brain, as shown in Table 1. The TV values estimated using these in vivo MR methods are in good agreement with post-mortem measurements summarized by Tofts, 2003. The summary measures show that the TV and VIP values differ substantially between cortical gray and intracortical white matter. Averaging across all of the gray and white, the ratio of VIP and TV—which is a measure or surface interactivity (FIG. 2)—is very similar. The TV in the sub-cortical regions is similar to the gray matter but the VIP in these regions is higher. Hence, the ratio of VIP and TV in sub-cortical regions is higher than in cortex and intracortical white matter.

These comparisons are coarse, and even in preliminary analyses we have seen substantial variations across gray matter regions, white matter tracts, and between subjects. We describe some of these differences below.

TABLE 1

Comparison of tissue volume (TV) and volume of interacting protons (VIP) values and their ratios in brain gray matter, brain white matter and in subcortical brain regions of 16 normal subjects.

|        | White matter | Gray matter | Thalamus | Caudate | Putamen |
|--------|--------------|-------------|----------|---------|---------|
| TV     | 0.285        | 0.178       | 0.2      | 0.18    | 0.19    |
| VIP    | 0.136        | 0.083       | 0.106    | 0.097   | 0.103   |
| VIP/TV | 0.481        | 0.49        | 0.544    | 0.55    | 0.55    |

Additional Measures of Reliability

To estimate the SPGR measurements reliability, they were repeated at each flip angle four times. Using a bootstrap procedure, the reliability (standard error) of the derived T1 value was ~0.01. A direct comparison between the 1.5 T and 3 T scanner of the gold standard $T_1$ map and the SPGR RF corrected $T_1$ maps showed that the SPGR T1 map is precise and reliable, the correlation between the two methods is high with r ~0.9; no systematic offset was found between the two maps.

The TV map can be evaluated by comparing the ratio of the TV values with those published in the literature. The different tissues can be identified based on their $T_1$ values, and within each tissue type we can estimate the ratio of the water fraction. The measured ratios for CSF:gray matter:white matter are 100:80:69. These TV ratios are consistent with published values measured by MRI, NMR and in post-mortem brains (see Table 1 in Tofts, 2003). Within-subject repeated measurements of the TV, WIP and VIP maps are highly reliable (N=3, r~0.8-0.7), even when comparing measurements made at different magnetic field strengths (1.5 T and 3 T), or using different scanning parameters and coils (see FIG. 4).

The good repeatability is evidence that VIP methods are a quantitative brain measurement that can be interpreted even if instrumental parameters can vary. Furthermore, the TV repeatability (panel C of FIG. 4) confirms that the bias correction for the rf-coil receiver inhomogeneity is robust across coils. The WIP repeatability (panel B of FIG. 4) supports the assumption that $T_1$ values are a linear function of free and bound water $T_1$ values, which each have a known dependency on the magnetic field strength (see Theory above). Note that a similar result was achieved when comparing to 0.5 T (not shown).

Classifying brain tissues. Combining the proton density and T1 data into an VIP measure improves the ability to segment and classify brain tissues, as shown above in Table 1. Combining the VIP and TV values for segmentation adds information about the tissue and improves segmentation.

Figure 5:
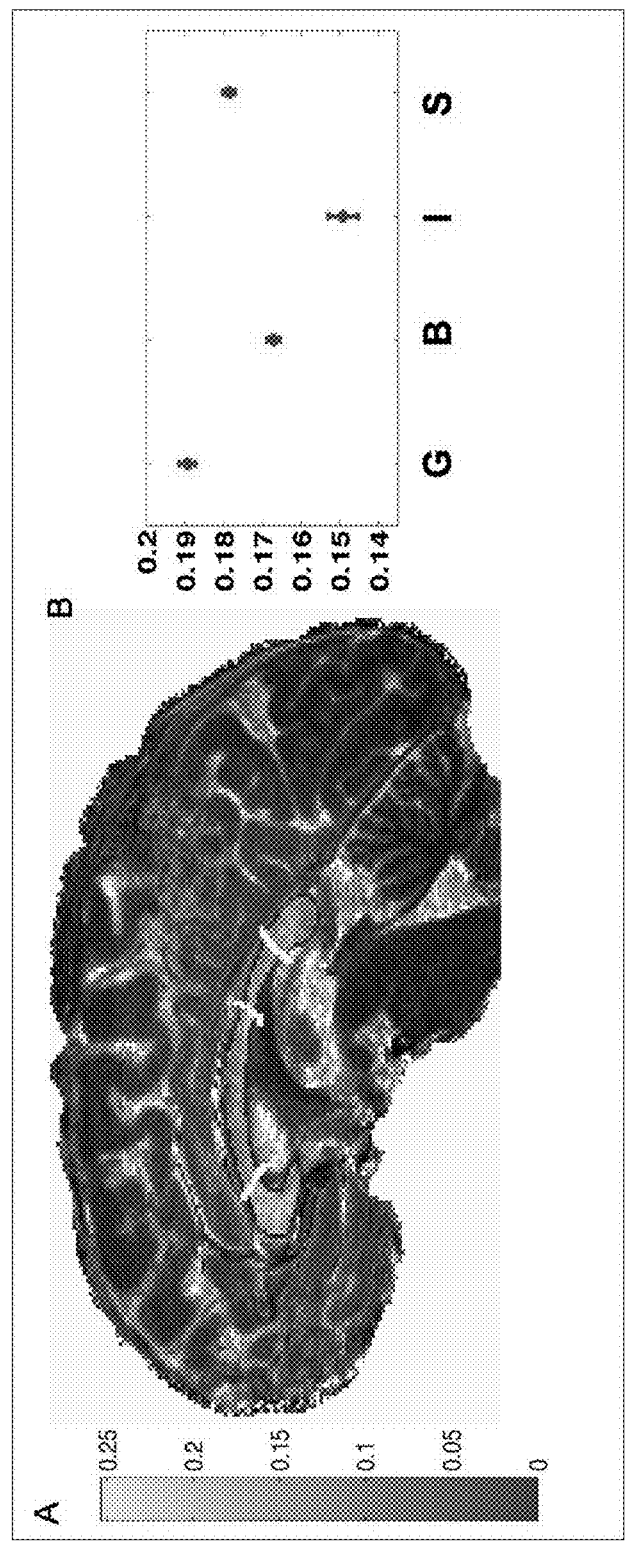
FIG. 5 illustrates an exemplary measurement of the volume of interacting protons (VIP) in a subject, as further detailed in Example 1. Panel A shows a $T_1$ sagittal view (background) overlaid by the measured VIP in the corpus callosum (color overlay). Panel B shows the VIP mean and standard error of four manually defined corpus callosum regions of this subject: the Genu (G), Body (B), Isthmus (I) and Splenium (S); they correspond to the regions in panel A ordered right to left. The white lines are the boundaries for region of interest analysis in panel B. Note the change of the VIP values along these regions.

The sensitivity of the VIP measure to different white matter regions is illustrated in FIG. 5. The background image in the left panel is a $T_1$ map of the mid-sagittal plane, showing the corpus callosum; the color overlay represents the VIP. The white lines are a manual segmentation of the corpus callosum into four main regions: the genu, body, isthmus and splenium (Aboitiz et al., 1992). The VIP values differ significantly between these callosal regions. Thus, the VIP measure is adequately sensitive to measure small region differences.

Comparison with Other Methods

In brain white matter both the myelin water fraction (MWF) and the bound pool fraction (BPF) are considered indicators of the myelin density. In theory these measurements as well as VIP and TV might probe different aspects of myelin. Hence, we examined the relationship between these measures. Recall that the MWF is derived from a fit to the $T_2$ relaxation. Several references provide tabulated data describing MWF, T1 and PD for various brain regions of interest (ROIs) in healthy subjects versus subjects suffering from multiple sclerosis (Whittall et al. 1997; Laule et al. 2007; Vavasour et al., 2007). Because the PD and T1 data are included, we can use the formula here to estimate the VIP for each of these ROIs. This enables a direct comparison between VIP and MWF. For these 20 ROIs, there is a correlation of 0.652 (P<0.002) between the VIP and the MWF values.

To compare BPF with VIP, we made additional measurements. Specifically, we implemented the pulse sequences and post-processing needed to measure BPF based on Yarnykh's method (Yarnykh and Yuan, 2004). The BPF and VIP values are correlated (r=0.59) across all brain voxels. The correlation between these measures is likely limited by the repeatability of each measure. The VIP reliability is higher than the MWF and BPF values, and the mean levels are generally consistent.

Characterization of Brain White Matter Tracts; Distinction from Neighboring White Matter Regions; distinction between different group of subjects, e.g., between children and adults, and Evaluation for Normal or Abnormal Brain Development We also compared between the VIP and TV with the standard diffusion MRI measurement of fractional anisotropy (FA) along the white matter tracts (see FIGS. 6 and 7). We found that within each tract the VIP has less variation than the FA, while the variation between subjects was greater for the VIP and TV. This result suggests that the VIP is a good candidate to study brain development as it has the statistic power to differentiate between different groups of subjects. Statistically we can show that the intraclass-correlation that defines the statistic power of a measurement is bigger for VIP and TV than FA (the current standard measure), and its value is close to 1 (the maximal value).

EXAMPLE 2

Correlation of Tissue Volume and Volume of Interacting Protons Measurements with Diffusion Tensor Imaging (DTI) Measurements to Facilitate DTI Measurement Interpretation in Brain White Matter Analysis All subjects from Example 1 were also scanned using diffusion tensor imaging (DTI). A DTI fiber tractography, visualization and analysis were performed using MR diffusion (Dougherty et al., 2005).

In diffusion imaging, the magnetic resonance signal (MR signal) is derived from the diffusion coefficient of protons. The diffusion coefficient is a physical parameter that directly reflects the physical tissue properties at a very fine scale well beyond the usual image resolution. Diffusion coefficients obtained at different times in the same subject or in different subjects can be compared without any need for standardization (Le Bihan et al., 2001). Therefore, quantitative analysis of the MR signal informs us about the statistical properties of very small structures, such as the lipid membranes, averaged across a voxel. By aggregating diffusion information across multiple voxels, it is possible to estimate the locations of major white matter tracts (Basser et al., 2000; Mori et al., 1999; Conturo et al., 1999). The diffusion of water within a voxel is influenced by many factors such as diffusion restriction, membrane permeability, hindrance, anisotropy, tortuosity and tissue inhomogeneity (Le Bihan et al., 2001). The membrane properties contribute to the diffusion signal, but other factors such as the presence of crossing fibers or overall fiber density also influence the diffusion signal. The heterogeneity of biological factors that drive the diffusion signal limits the interpretation of diffusion measurements (Beaulieu, 2002; Paus, 2010). This example illustrates the usefulness of integrating TV and VIP values with diffusion signals to aid in the interpretation of diffusion measurements.

Diffusion fractional anisotropy (FA) is regularly used as an index of white matter integrity. However it is agreed that FA measurement captures a range of geometric and microstructural properties, and it is unclear which biological factors account for the variation in FA measurements (Beaulieu, 2002; Paus, 2010).

To demonstrate a complementary nature of those measurements, VIP and FA values were compared along the corticospinal tract (CST, FIG. 6C shows the core fiber of the corticospinal tract) by plotting the weighted average of the VIP (FIG. 6C), FA (FIG. 6B), and non-water tissue volume (TV, FIG. 7) values, where the weight for each voxel was inversely proportional to its covariance (Mahalanobis) distance from the core fiber. The VIP and TV values increased monotonically along the corticospinal tract from its base in the brainstem to its superior portion near the cortex. The FA values along the same path were roughly constant and then dropped significantly as they passed near fibers from the corpus callosum (near node 40 in FIG. 6B). This region is part of the centrum semiovale where there is a large number of crossing fibers (Wedeen et al., 2008). The FA values dropped because of the loss of fiber direction coherence, which, however, did not substantially affect the VIP or TV values. Hence, MRI applications that target to elucidate white matter development, brain connectivity and tracking of white matter fibers and pathways can benefit by combining VIP and TV values with FA values.

Correlation of Brain White Matter Microstructure with Cognitive Abilities in a Subject.

Another potential application of the combined values of VIP, TV and FA measurements concerns the pattern of differences between subjects. FIGS. 6B and 6C illustrate that the subjects are distinguished by their consistent VIP profile along the full trajectory of the axon bundles. These VIP values are stable within 1% (N=4), while the FA values curve for the different subjects and intersect multiple times (see FIG. 6B). Thus, the VIP values may characterize a property of the white matter that reliably distinguishes individuals offering the possibility for characterizing the relationship between cognitive abilities such as reading ability or writing ability and white matter microstructure.

Figure 6:
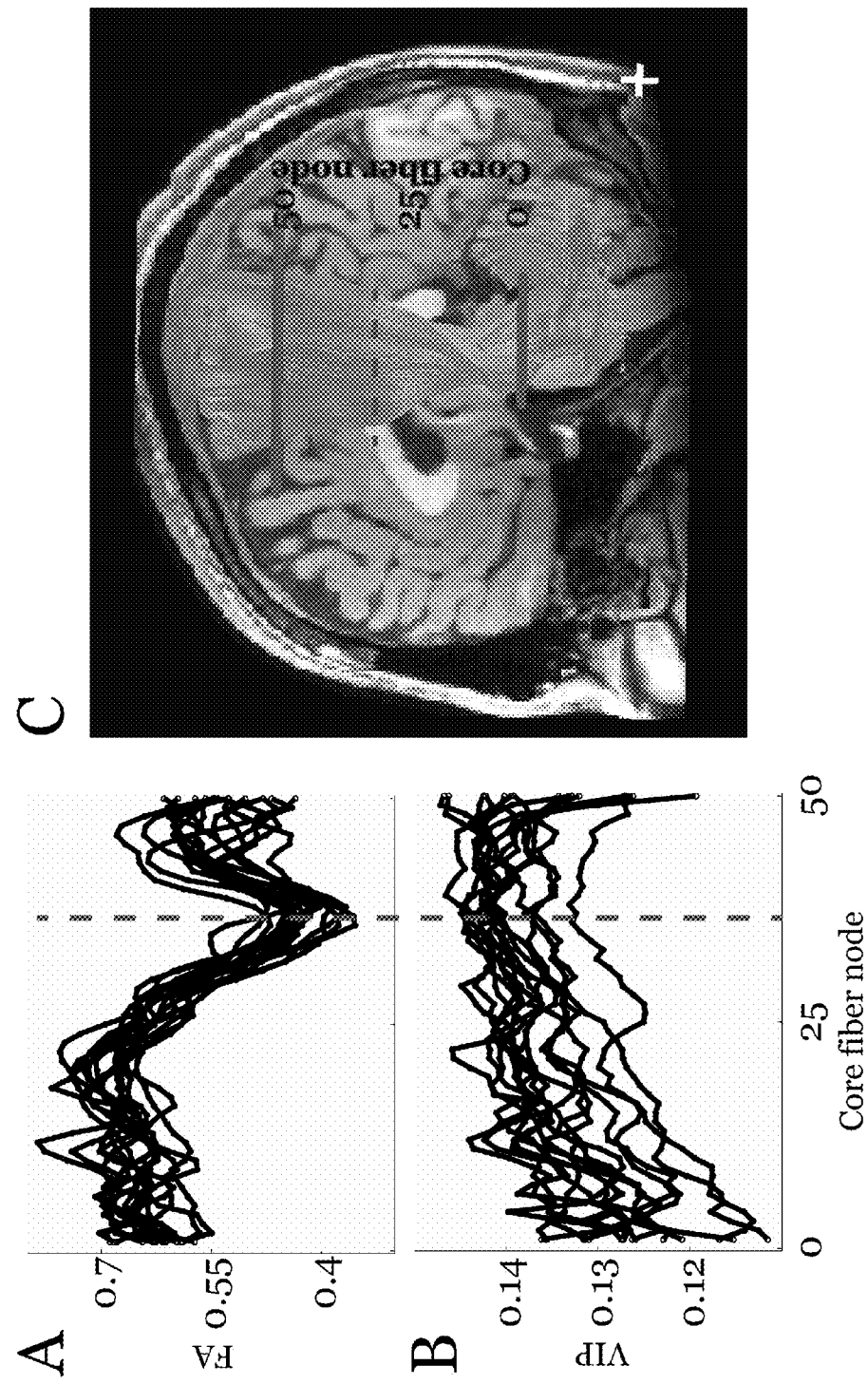
FIG. 6 illustrates a comparative analysis of volume of interacting protons (VIP) and diffusion fractional anisotropy (FA) values in the corticospinal tract (CST), as further detailed in Example 2. Panel C shows an approximation of the CST by deterministic diffusion tensor imaging (DTI) tractography, as shown in blue. Panels A and B show the mean VIP and FA values as measured at different positions along the CST in 16 different subjects. The FA value declines in the region where the CST and callosal fibers intersect (red line). Notice the consistent difference between subjects in the VIP but not FA, values.

FIG. 6 and FIG. 7 show the usefulness of integrating TV and VIP values with diffusion signals to aid in the interpretation of diffusion measurements.

EXAMPLE 3

Analysis of a Subjects Suffering from Multiple Sclerosis in Comparison to 16 Control Subjects In order to examine the capability of VIP methods to be used as an assessment tool in clinical white matter abnormalities, one patient who had been diagnosed with multiple sclerosis ('MS subject') was scanned, and VIP as well as TV maps were obtained, as described supra. In addition 11 healthy subjects ('control subjects') were scanned, and VP as well as TV maps were obtained for them, as described supra. The VIP and TV maps of the MS subject were compared with the VIP and TV maps of the 11 control subjects. FIG. 8a illustrates the MS subject's VIP map. The colored areas indicate the areas that differ from the control subjects with Z scores <3.5. The color code shows the percentage change in the VIP value in those regions. We found that this analysis enabled an automatic localization of the MS lesions areas (colored areas). FIG. 8b illustrates the MS subject's TV map. Here a difference between the maps can be noted, as they measure different white matter physical properties. Moreover, in addition to lesions areas some of the colored regions are located in the gray matter and in white matter regions that appear as normal white matter in standard T2 weighted image, suggesting that the method can also detect other types of abnormalities than the current standard measurement.

FIG. 11 shows the values of FA, TV, VIP and VIP/TV ratio for three MS subjects (A, B and C) along a white matter tract, the Inferior longitudinal fasciculus (ILF). Each subject's values (red line) are shown in different columns. The normal population values (N=16) along that same tract are plotted in gray. We can see that MS subject A's lesions are not as severe as those of MS subject C. Therefore, the images illustrate the capability of the methods to evaluate difference in lesions severity. The fact that MS subject B's TV values are constant but under the norm illustrate the capability of the method to define and detect abnormal white matter tissue, even if it had appeared normal when other imaging methods were used. All MS subjects' ratios of VIP/TV are greater then those of the control subjects. This result suggests that beside tissue loss the method can also measure change in the underline disease tissue. Please note that FA cannot be used to draw similar conclusion (FIG. 11, first row).

EXAMPLE 4

Characterization of White Matter Tracts

Figure 9:
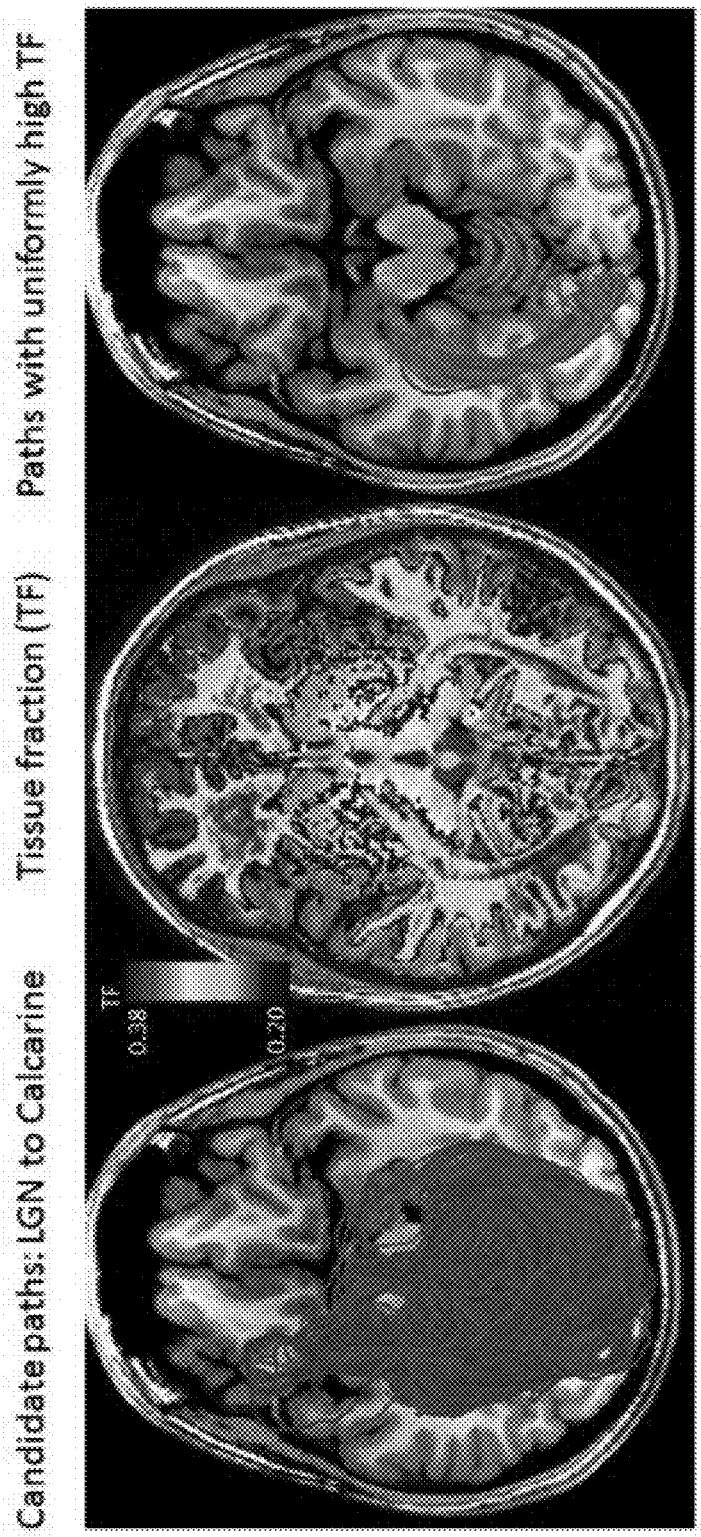
FIG. 9 shows that optic radiation paths have a distinct tissue signature, as further detailed in Example 4. The optic radiation, also known as the geniculo-calcarine tract, is a collection of axons from relay neurons in the lateral geniculate nucleus (LGN) carrying visual information to the primary visual cortex (V1) along the calcarine fissure. There is one such tract on each side of the brain. The diffusion tensor imaging (DTI) candidate paths on the left are a large group whose endpoints are in the LGN and V1. Selecting only paths that have uniformly high tissue fraction (middle) produces an excellent estimate of the optic radiation (right).

Methods of the present invention have furthermore demonstrated usefulness in characterizing white matter tracts and in distinguishing white matter tracts from neighboring white matter regions. As illustrated in FIG. 9, optic radiation paths have a distinct tissue signature. The optic radiation, also known as the geniculo-calcarine tract, is a collection of axons from relay neurons in the lateral geniculate nucleus (LGN) carrying visual information to the primary visual cortex (V1) along the calcarine fissure. There is one such tract on each side of the brain. The diffusion tensor imaging (DTI) candidate paths on the left are a large group whose endpoints are in the LGN and V1. Selecting only paths that have uniformly high tissue volume (middle) produces an excellent estimate of the optic radiation (right). The DTI data tractography generated many more fiber candidates than the real white matter set. The true fibers are selected using the quantitative information of the TV and VIP map. The TV map allows to select only the fibers that maintain a constant tissue signature. The method allows to define the true fiber in the brain from the big (wrong) set that the conventional methods provide. This approach also allows to identify the true signature (TV and VIP) per fiber set.

EXAMPLE 5

Identification of Brain Development in Children Versus Adults

Figure 10:
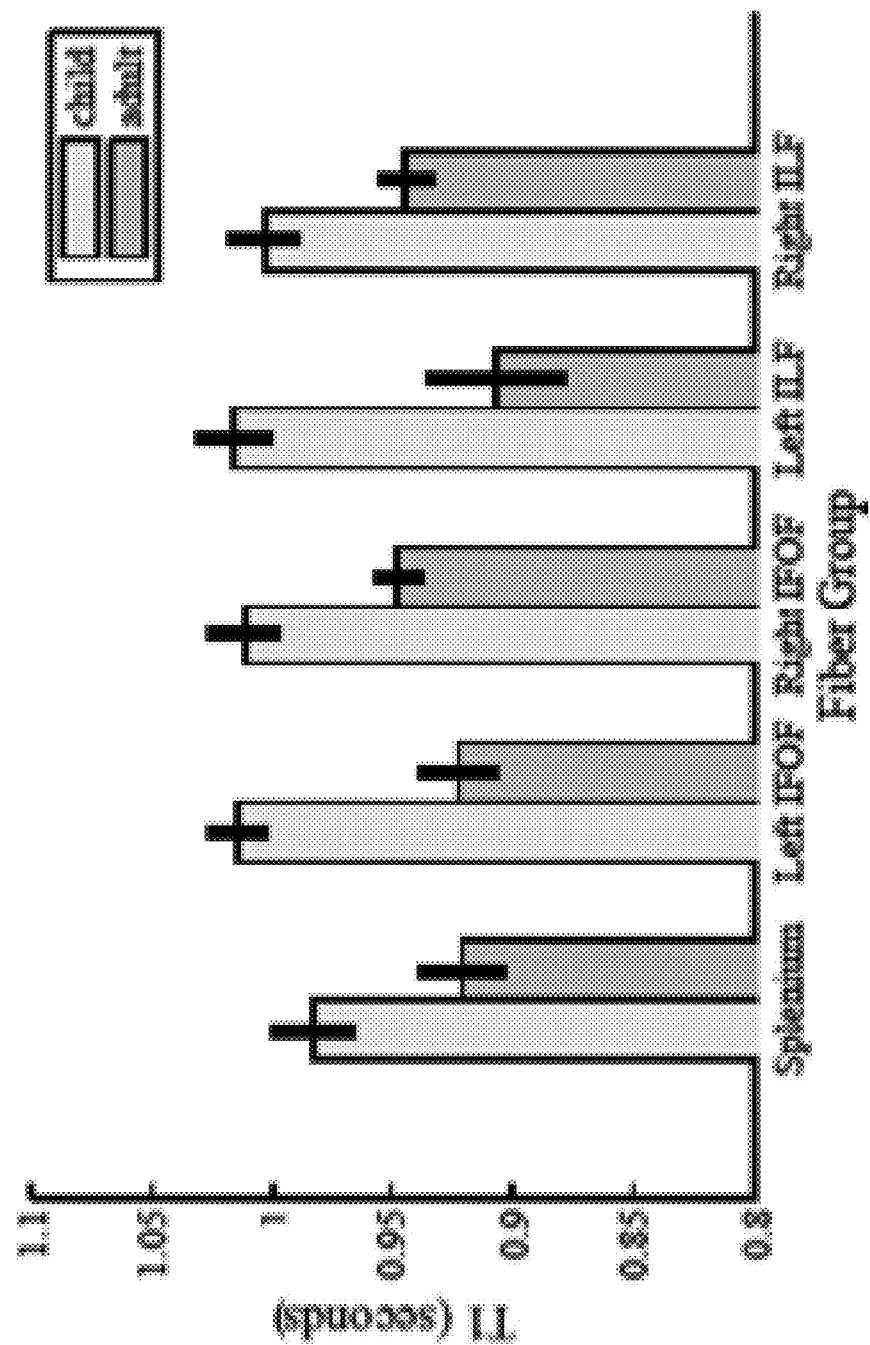
FIG. 10 illustrates differential development of brain white matter tracts in children and adults in various brain regions, as further detailed in Example 5. T1 values in visual white matter from 8-10 year olds (N=8) were 3-5 SEM larger than from adults (N=16) in all major visual tracts.

FIG. 10 illustrates differential development of brain white matter tracts in children and adults: T1 values in visual white matter from 8-10 year olds (N=8) were 3-5 SEM larger than from adults (N=16) in all major visual tracts.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

REFERENCES

Aboitiz F et al. (1992) "Fiber composition of the human corpus callosum." *Brain Res* 598:143-53.
Barral J K et al. (2010) "A robust methodology for in vivo T(1) mapping." *Magn Reson Med* 64: 1057-1067.
Basser P J et al. (1994) "MR diffusion tensor spectroscopy and imaging." *Biophys J* 66: 259-267.
Basser P J et al. (2000). "In vivo fiber tractography using DT-MRI data." *Magn Reson Med* 44:625-632.
Beaulieu C (2002). "The basis of anisotropic water diffusion in the nervous system—a technical review". *NMR in biomedicine* 15:435-455.
Bloembergen N et al. (1948) "Relaxation effects in nuclear magnetic resonance absorption". *Phys Rev* 73: 679-714.
Bot J C J et al. (2004). "Spinal cord abnormalities in recently diagnosed MS patients: Added Value of spinal MRI examination." *Neurology* 62: 226-233.
Bottomley P A. et al. (1984) "A review of normal tissue hydrogen NMR relaxation times and relaxation mechanisms from 1-100 MHz: dependence on tissue type, NMR frequency, temperature, species, excision, and age." *Med Phys* 11:425-48.
Brauser D (2012). "Brain Changes Found in Youth with Schizophrenia, Psychosis" *Arch Gen Psych* 69:16-26.
Caluccia, L. and F. C. (2009). "Proton longitudinal relaxation coupling in dynamically heterogeneous soft systems." *Progress in Nuclear Magnetic Resonance Spectroscopy* 55: 296-323.
Chang L C et al. (2008). "Linear least-squares method for unbiased estimation of T1 from SPGR signals." *Magn Reson Med* 60:496-501.
Chen Z et al. (2011). "Mapping the brain in type II diabetes: voxel-based morphometry using DARTEL". *Eur J Radiol*, available on-line May 6, 2011, still in press.
Conturo T E et al. (1999). "Tracking neuronal fiber pathways in the living human brain." *PNAS* 96:10422-10427.
Corouge I et al. (2004). "Statistical Shape Model of Individual Fiber Tracts Extracted from Diffusion Tensor MRI". *Lecture Notes in Computer Science* 3217: 671-679.
Deoni S C et al. (2004) "Determination of optimal angles for variable mutation proton magnetic spin-lattice, T1, and spin-spin, T2, relaxation times measurement." *Magn Reson Med* 51:194-199.
Deoni S C (2007) "High-resolution T1 mapping of the brain at 3 T with driven equilibrium single pulse observation of T1 with high-speed incorporation of RF field inhomogeneities (DESPOT1-HIFI)." *J Magn Reson Imaging* 26:1106-1111.
Dougherty R F et al. (2005). "Occipital-callosal pathways in children: Validation and atlas development." *Ann NY Acad Sci* 1064: 98-112.

Dula A N et al. (2009) Multiexponential T2, magnetization transfer and quantitative histology in white matter tracts of rat spinal cord. *Proceedings of the 17th Annual Meeting of ISMRM*, Honolulu, US. International Society for Magnetic Resonance in Medicine.

Fischl B & Dale A M (2000). "Measuring the thickness of the human cerebral cortex from magnetic resonance images." *PNAS* 97:11050-11055.

Fram E K et al. (1987) "Rapid calculation of T1 using variable flip angle gradient refocused imaging". *Magn reson imag* 5: 201-208.

Franc D T et al. (2011). "High connectivity between reduced cortical thickness and disrupted white matter tracts in long-standing Type-1 diabetes". *Diabetes* 60:315-319.

Friston K J & Ashburner J (2004) "Generative and recognition models for neuroanatomy". *NeuroImage* 23:21-24.

Fullerton G D et al. (1984) "Frequency dependence of magnetic resonance spin-lattice relaxation of protons in biological materials." *Radiology* 151:135-138.

Gao J et al. (2011). "Possible retrogenesis observed with fiber tracking: an anteroposterior pattern of white matter disintegrity in normal aging and alzheimer's disease" *J Alzheim Dis* 26:47-58.

Halle B (2006). "Molecular theory of field-dependent proton spin-lattice relaxation in tissue." *Magn Reson Med* 56:60-72.

Hopkins A L et al. (1986) "Multiple field strength in vivo T1 and T2 for cerebrospinal fluid protons" *Magn Reson Med* 3:303-311.

Kurtzke J F (1983). "Rating neurologic impairment in multiple sclerosis: an expanded disability status scale (EDSS)." *Neurology* 33:1444-52.

Laule C I M et al. (2007). "Long T2 water in multiple sclerosis: what else can we learn from multi-echo T2 relaxation?" *J Neurol* 254:1579-87.

Le Bihan D et al. (2001). "Diffusion tensor imaging: concepts and applications" *J Magn Reson Imag* 13:534-546.

Mansfield P & Morris P G (1982) "NMR imaging in biomedicine". Academic Press, London, England.

Mark L P et al. (1993). "Limbic system anatomy: an overview". *Am J Neuroradiol* 14:349-352.

MacKay A et al. (1994) "In vivo visualization of myelin water in brain by magnetic resonance". *Magn Reson Med* 31: 673-677.

Milhaud J (2004). "New insights into water-phospholipid model membrane interactions". *Biochim biophys act* 1663: 19-51.

Mori S et al. (1999) "Three-dimensional tracking of axonal projections in the brain by magnetic resonance imaging". *Annals of neurology* 45:265-269.

Moseley M E et al. (1990) "Early detection of regional cerebral ischemia in cats: comparison of diffusion- and T2-weighted MRI and spectroscopy." *Magn Reson Med* 14: 330-346.

Nelson T R & Tung S M (1987). "Temperature dependence of proton relaxation times in vitro." *Magn Reson Imaging* 5:189-99.

Norton W T & Autilio L A (1966). "The lipid composition of purified bovine brain myelin". *J Neurochem* 13:213-222.

Noterdaeme O et al. (2009). "Intensity correction with a pair of spoiled gradient recalled echo images." *Phys Med Biol* 54(11): 3473-89.

Paus T (2010). Growth of white matter in the adolescent brain: myelin or axon? *Brain and cognition* 72:26-35.

Polman C H et al. (2005). "Diagnostic criteria for multiple sclerosis: 2005 revisions to the "McDonald Criteria"." *Ann Neurol* 58:840-6.

Rooney W D et al. (2007). "Magnetic field and tissue dependencies of human brain longitudinal 1H2O relaxation in vivo." *Magn Reson Med* 57:308-18.

Ryan C M (2009). "Diabetes Mellitus and Neurocognitive Dysfunction", Elsevier, Inc., $2^{nd}$ edition: 2974-3003.

Schumann et al. (2010) "Longitudinal magnetic resonance imaging study of cortical development through early childhood in autism". *J Neurosci* 30:4419-4427.

Stikov N et al. (2011) "Bound pool fractions complement diffusion measures to describe white matter micro and macrostructure". *NeuroImage* 54: 1112-1121.

Tofts P (2003). "Quantitative MRI of the brain: measuring changes cause by disease". *John Wiley & Sohns*, $1^{st}$ edition.

Vavasour I M et al. (2007) "Multi-parametric MR assessment of T(1) black holes in multiple sclerosis: evidence that myelin loss is not greater in hypointense versus isointense T(1) lesions." *J Neurol* 254:1653-1659.

Wakana S et al. (2004). Fiber tract-based atlas of human white matter anatomy. *Radiology* 230:77-87.

Wedeen V J (2008). "Diffusion spectrum magnetic resonance imaging (DSI) tractography of crossing fibers." *NeuroImage* 41:1267-1277.

Whittall K P et al. (1997) "In vivo measurement of T2 distributions and water contents in normal human brain." *Magn Reson Med* 37:34-43.

Yarnykh V L & Yuan C (2004) "Cross-relaxation imaging reveals detailed anatomy of white matter fiber tracts in the human brain." *Neuroimage* 23:409-24.

Zimmerman, J. R. and W. E. Brittin (1957). "Nuclear Magnetic Resonance Studies in Multiple Phase Systems Lifetime of a Water Molecule in an Adsorbing Phase on Silica Gel." *J. Phys. Chem.* 61(10): 1328-1333.

What is claimed is:

1. A computer-implemented method of noninvasively detecting structural abnormalities in a subject's soft tissue, the method comprising
    acquiring, via a magnetic resonance imaging system, magnetic resonance images and magnetic resonance imaging (MRI) parameters from said soft tissue and
    calculating, by a computer, non-water tissue volume (TV) and volume of interacting protons (VIP) values in said subject's soft tissue from said magnetic resonance imaging parameters by using algorithms that combine proton density (PD) and T1 map data,
    calculating, by a computer, said subject's water pool and non-water pool concentrations from said subject's TV and VIP values,
    comparing, by a computer, said subject's water pool and non-water pool concentrations to water pool and non-water pool concentrations from soft tissue TV and VIP values obtained from a healthy control subject,
    determining, by a computer, a difference between said test subject's water pool as well as non-water pool concentrations and said healthy control subject's water pool and non-water pool concentrations; and determining, by a computer, structural abnormalities in said test subject's soft tissue responsive to said difference.

2. The method of claim 1, wherein said structural abnormalities are changes in tissue volume.

3. The method of claim 1, wherein said structural abnormalities are changes in myelination.

4. The method of claim 1, wherein said structural abnormalities are changes in tissue microstructure.

5. The method of claim 1, wherein the soft tissue is cartilage.

6. The method of claim 1, wherein the soft tissue is a fatty tissue.

7. The method of claim 1, wherein the soft tissue is muscle tissue.

8. The method of claim 1, wherein the soft tissue is a peripheral nerve tissue.

9. The method of claim 1, wherein the soft tissue is a central nervous tissue.

10. The method of claim 9, wherein said central nervous tissue is brain white matter.

11. The method of claim 9, wherein said central nervous tissue is brain gray matter.

12. The method of claim 9, wherein said central nervous tissue is ventricles carrying cerebrospinal fluid.

13. The method of claim 1, wherein said subject may suffer from a neurological disease.

14. The method of claim 1, wherein said subject may suffer from a neurodegenerative disease.

\* \* \* \* \*